United States Patent [19]
Thornton et al.

[11] Patent Number: 5,985,593
[45] Date of Patent: Nov. 16, 1999

[54] COMPOSITIONS AND METHODS FOR ENZYMATIC DECONTAMINATION

[75] Inventors: Charles G. Thornton, Gaithersburg; Kerry M. MacLellan, Belair, both of Md.

[73] Assignee: Integrated Research Technology, L.L.C., Baltimore, Md.

[21] Appl. No.: 08/943,338

[22] Filed: Oct. 3, 1997

Related U.S. Application Data

[60] Provisional application No. 60/028,470, Oct. 11, 1996.

[51] Int. Cl.$^6$ ............................... C12Q 1/02; C12N 1/06; C12N 9/00; A01N 37/30
[52] U.S. Cl. ........................... 435/29; 435/34; 435/173.2; 435/173.7; 435/173.9; 435/253.1; 435/259; 514/556
[58] Field of Search .................................. 435/29, 34, 15, 435/18, 23, 26, 173.2, 173.7, 173.9, 200, 206, 207, 208, 210, 211, 220, 221, 223, 225, 270, 253.1, 259; 514/556

[56] References Cited

U.S. PATENT DOCUMENTS

| | | | |
|---|---|---|---|
| 3,850,798 | 11/1974 | Sjöquist | 530/350 |
| 3,914,436 | 10/1975 | Nakadai et al. | 426/46 |
| 4,366,250 | 12/1982 | Jallageas et al. | 435/280 |
| 4,517,290 | 5/1985 | Iwasa et al. | 435/7 |
| 4,603,108 | 7/1986 | Bascomb | 435/34 |
| 4,652,517 | 3/1987 | Scholl et al. | 435/5 |
| 4,693,888 | 9/1987 | Miyahara et al. | 424/49 |
| 4,828,998 | 5/1989 | Wöhner et al. | 435/206 |
| 4,994,378 | 2/1991 | Berger et al. | 435/29 |
| 5,077,206 | 12/1991 | Cheetham et al. | 435/99 |
| 5,185,242 | 2/1993 | Keating et al. | 435/6 |
| 5,236,955 | 8/1993 | Gordon | 514/557 |
| 5,250,306 | 10/1993 | McCleary et al. | 426/52 |
| 5,356,800 | 10/1994 | Jaquess | 435/188 |
| 5,366,755 | 11/1994 | Timonen et al. | 426/658 |
| 5,374,545 | 12/1994 | Liu et al. | 435/183 |
| 5,418,156 | 5/1995 | Stosz et al. | 435/200 |
| 5,530,187 | 6/1996 | Lamb et al. | 800/279 |
| 5,556,781 | 9/1996 | Kubota et al. | 435/200 |
| 5,573,915 | 11/1996 | Barry, III et al. | 435/6 |
| 5,658,749 | 8/1997 | Thornton | 435/29 |
| 5,672,482 | 9/1997 | Kushibe et al. | 435/15 |
| 5,723,328 | 3/1998 | Dalboege et al. | 435/209 |
| 5,776,694 | 7/1998 | Scheiness et al. | 435/6 |
| 5,783,410 | 7/1998 | He et al. | 435/34 |
| 5,811,148 | 9/1998 | Chiu et al. | 426/548 |

FOREIGN PATENT DOCUMENTS

| | | | |
|---|---|---|---|
| 0 181 562 | 5/1986 | European Pat. Off. | C12N 9/14 |
| 5-23167 | 2/1993 | Japan | C12M 1/12 |
| 1048887 | 11/1966 | United Kingdom | C12D 11/00 |
| WO 95/22510 | 9/1995 | WIPO | A61K 31/19 |
| 95/27076 | 10/1995 | WIPO | C12Q 1/00 |
| WO 95/27076 | 10/1995 | WIPO | C12Q 1/00 |
| 95/31534 | 11/1995 | WIPO | C12N 9/42 |

OTHER PUBLICATIONS

Dubourdieu, D., et al., "Investigations of an industrial β–D–glucanase from *Trichoderma harzianum*," *Carbohydrate Res.* 144:277–287 (1985), No Month Found.

Aber, V.R. et al., "Quality Control in Tuberculosis Bacteriology: 1. Laboratory Studies on Isolated Positive Cultures and the Efficiency of Direct Smear Examination," *Tubercle* 61:123–133 (1980).

Andrews, B.A. and J.A. Asenjo, "Synthesis and Regulation of Extracellular β(1–3)Glucanase and Protease by Cytophaga sp. in Batch and Continuous Culture," *Biotechnol. & Bioengineering* 28:1366–1375 (1986).

Barman, T.E., *Enzyme Handbook*, vol. II, Springer–Verlag, Berlin, Germany, pp. 560–594 (1969).

Barry, III, C.E. and K. Mdluli, "Drug sensitivity and environmental adaptation of mycobacterial cell wall components," *Trends In Microbiol.* 4(7):275–281 (Jul. 1996).

Calandra, G.B. and R.M. Cole, "Lysis and Protoplast Formation of Group B Streptococci by Mutanolysin," *Infect. & Immunity* 28(3):1033–1037 (Jun. 1980).

Chapin, K., "Clinical Microscopy," In: *Manual of Clinical Microbiology*, Sixth Ed., Murray, P.R. et al., eds., ASM Press, Washington, DC, pp. 33–51 (May 1995).

Cisani, G. et al., "High–Level Potentiation of Lysostaphin Anti–Staphylococcal Activity by Lysozyme," *Antimicrobial Agents & Chemotherapy* 21(4):531–535 (Apr. 1982).

Dixon, M. et al., "Enzyme Mechanisms," In: *Enzymes*, Third Ed., Dixon, M. et al., eds., Academic Press, Inc., New York, NY, pp. 300–317 (1979).

Dixon, M. et al., "Table of Enzymes," In: *Enzymes*, Third Ed., Dixon, M. et al., eds., Academic Press, Inc., New York, NY, pp. 860–873 (1979).

Eiglmeier, K. et al., "Use of an ordered cosmid library to deduce the genomic organization of *Mycobacterium leprae*," *Molec. Microbiol.* 7(2):197–206 (1993).

Espinel–Ingroff, A. and M.A. Pfaller, "Antifungal Agents and Susceptibility Testing," In: *Manual of Clinical Microbiology*, Sixth Ed., Murray, P.R. et al., eds., ASM Press, Washington, DC, pp. 1405–1414 (May 1995).

Ezaki, T. and S. Suzuki, "Achromopeptidase for Lysis of Anaerobic Gram–Positive Cocci," *J. Clin. Microbiol.* 16(5):844–846 (Nov. 1982).

Falkinham, III, J.O., "Epidemiology of Infection by Nontuberculous Mycobacteria," *Clin. Microbiol. Rev.* 9(2):177–215 (Apr. 1996).

Funke, G. et al., "Clinical Microbiology of Coryneform Bacteria," *Clin. Microbiol. Rev.* 10(1):125–159 (Jan. 1997).

Gebre, N. et al., "Improved microscopical diagnosis of pulmonary tuberculosis in developing countries," *Transac. Royal Soc. Trop. Med. Hyg.* 89:191–193 (Mar.–Apr. 1995).

(List continued on next page.)

*Primary Examiner*—Kathleen K. Fonda
*Assistant Examiner*—Marjorie A. Moran
*Attorney, Agent, or Firm*—Sterne, Kessler, Goldstein & Fox P.L.L.C.

[57] ABSTRACT

The present invention is related to a method for the enzymatic decontamination of specimens as a means to control microbiological contamination. The compositions and methods of the invention are especially useful to eliminate non-gram negative contaminants of samples being processed for microbiological analysis.

117 Claims, 14 Drawing Sheets

OTHER PUBLICATIONS

Goren, M.B., "Mycobacterial Lipids: Selected Topics," *Bacteriological Rev.* 36(1):33–44 (Mar. 1972).

Inderlied, C.B. and M. Salfinger, "Antimicrobial Agents and Susceptibility Tests Mycobacteria," In: *Manual of Clinical Microbiology*, Sixth Ed., Murray, P.R. et al., ASM Press, Washington, DC, pp. 1385–1404 (May 1995).

Joklik, W.K. et al., "Composition, Structure, and Biosynthesis of the Bacterial Cell Envelope and Energy Storage Polymers," In: *Zinsser Microbiology*, Seventeenth Ed., Joklik, W.K. et al., eds., Appleton–Century–Crofts, New York, NY, pp. 106–134 (1980).

Joklik, W.K. et al., "General Characteristics of Fungi," In: *Zinsser Microbiology*, Seventeenth Ed., Joklik, W.K. et al., eds., Appleton–Century–Crofts, New York, NY, pp. 1326–1337 (1980).

Kobayashi, R. et al., "Preparation and Evaluation of an Enzyme which Degrades Yeast Cell Walls," *Eur. J. Appl. Microbiol. Biotechnol.* 15:14–19 (Jun. 1982).

Kubica, G.P. et al., "Sputum Digestion and Decontamination with N–Acetyl–L–Cysteine–Sodium Hydroxide for Culture of Mycobacteria," *Am. Rev. Resir. Dis.* 87:775–779 (1963).

Lederer, E., "Glycolipids of Mycobacteria and Related Microorganisms," *Chem. Phys. Lipids* 1:294–315 (1967).

Lederer, E., "The Mycobacterial Cell Wall," *Pure Appl. Chem.* 25:135–165 (1971).

Lehninger, A.L., *Biochemistry: The Molecular Basis of Cell Structure and Function*, Chapters 12 and 13, Worth Publishers, Inc., New York, NY, pp. 249–277 (1970).

Merck Index, Eleventh Ed., 1935. Cefotaxime, Budavari, S. et al., eds., pp. 296–297 (1989).

Metcalf, R.H. and R.H. Deibel, "Differential Lytic Response of Enterococci Associated with Addition Order of Lysozyme and Anions," *J. Bacteriol.* 99(3):674–680 (Sep. 1969).

Nightingale, S.D. et al., "Incidence of *Mycobacterium avium–intracellulare* Complex Bacteremia in Human Immunodeficiency Virus–Positive Patients," *J. Infect. Dis.* 165:1082–1085 (1992).

Scott, J.H. and R. Schekman, "Lyticase: Endoglucanase and Protease Activities That Act Together in Yeast Cell Lysis," *J. Bacteriol.* 142(2):414–423 (May 1980).

Stone, B.L. et al., "The Diagnostic Yield of Acid–Fast–Bacillus Smear–Positive Sputum–Specimens," *J. Clin. Microbiol.* 35(4):1030–1031 (Apr. 1997).

Suzuki, K. et al., "*Serratia marcescens*–Lytic Enzyme Produced by Micromonospora sp. Strain No. 152," *Agric. Biol. Chem.* 49(6):1719–1726 (Jun. 1985).

Tsubone, K. et al., "Relation between Structure and Antimicrobial Activity of 2–(N,N,N,–Trialkylammonio)alkyl Hydrogen Phosphates," *J. Pharmaceut. Sci.* 80(5):441–444 (May 1991).

Voss, J.G., "Effects of Organic Cations on the Gram–negative Cell Wall and Their Bactericidal Activity with Ethylenediamine–tetra–acetate and Surface Active Agents," *J. Gen. Microbiol.* 48:391–400 (Sep. 1967).

Wadstrøm, T. and O. Vesterberg, "Studies on Endo–β–N–Acetylglucosaminidase, Staphylolytic Peptidase, and N–Acetylmuramyl–L–Alanine Amidase, in Lysostaphin and from *Staphylococcus Aureus*," *Acta Path. Microbiol. Scand.* 79(sec. B):248–264 (1971).

Wayne, L.G. and H.A. Sramek, "Agents of Newly Recognized or Infrequently Encountered Mycobacterial Diseases," *Clin. Microbiol. Rev.* 5(1):1–25 (Jan. 1992).

Yao, J.D.C. and R.C. Moellering, Jr., "Antibacterial Agents," In: *Manual of Clinical Microbiology*, Sixth Ed., Murray, P.R. et al., ASM Press, Washington, DC, pp. 1281–1307 (May 1995).

Enzyme Nomenclature, Recommendations (1972) of the International Union of Pure and Applied Chemistry and the International Union of Biochemistry, American Elsevier Scientific Publishing Co., New York, NY, pp. 212–228 ((1973).

Public Health Mycobacteriology: A Guide for the Level III Laboratory, Kent, P. and G.P. Kubica, eds., U.S. Dept. of Health and Human Services, pp. 31–47 (1985).

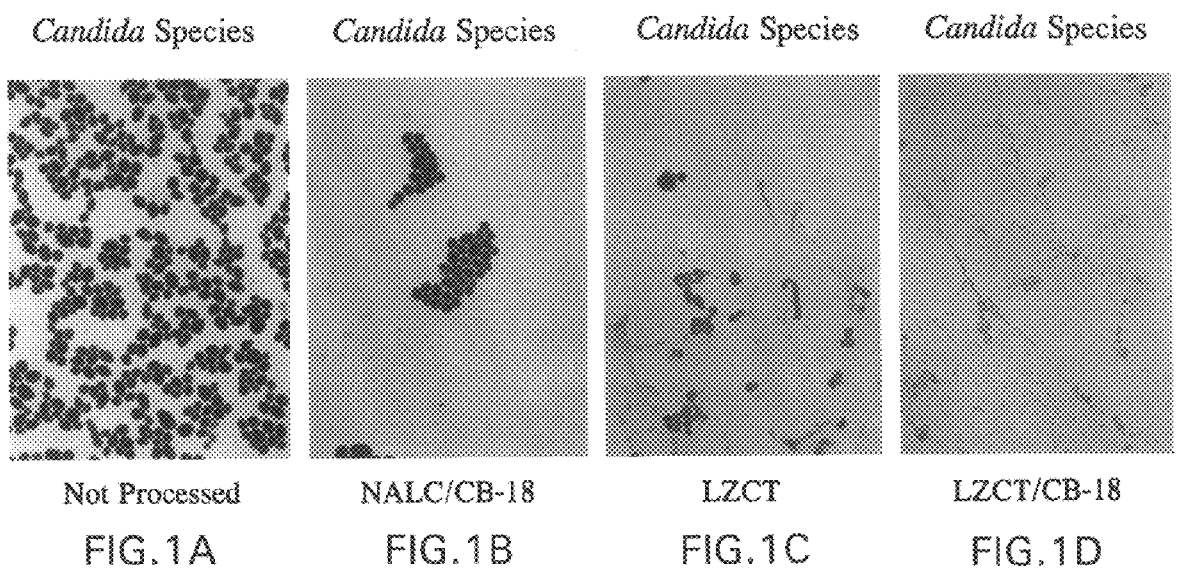

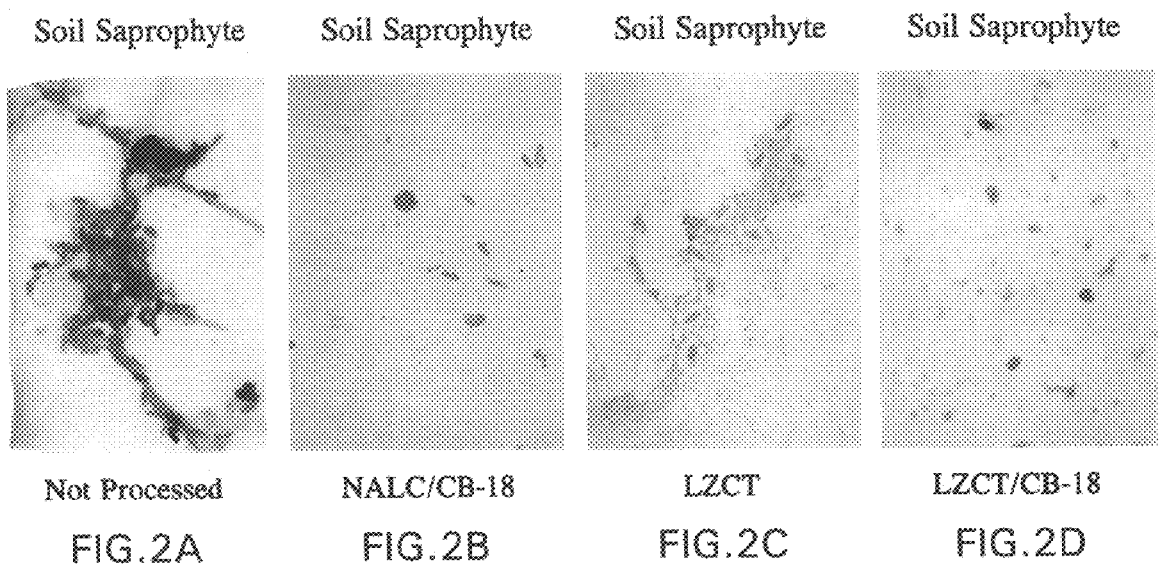
FIG.2A Not Processed
FIG.2B NALC/CB-18
FIG.2C LZCT
FIG.2D LZCT/CB-18

*Aspergillus* Species   *Aspergillus* Species   *Aspergillus* Species   *Aspergillus* Species
 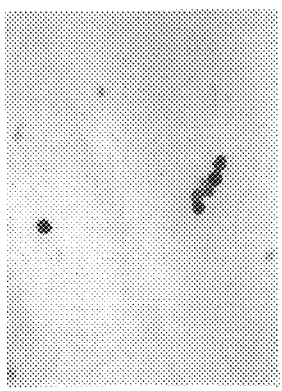 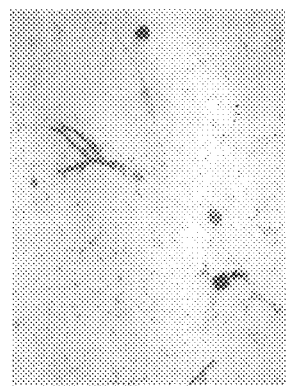 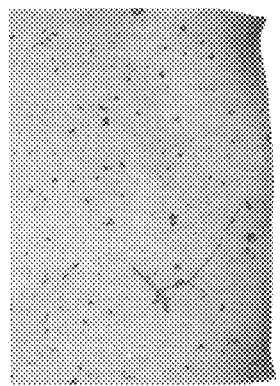
Not Processed             NALC/CB-18              LZCT                    LZCT/CB-18
FIG.3A                    FIG.3B                  FIG.3C                  FIG.3D

*Staphylococcus aureus*

Not Processed

*Staphylococcus aureus*

NALC/CB-18

*Staphylococcus aureus*

LZCT

*Staphylococcus aureus*

LZCT/CB-18

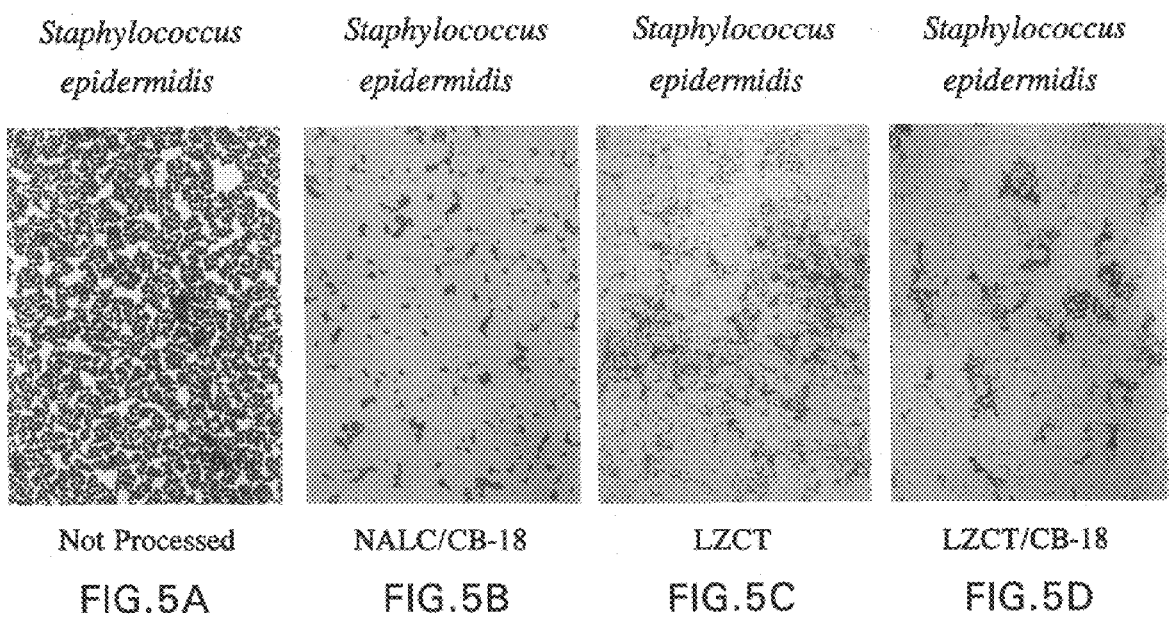

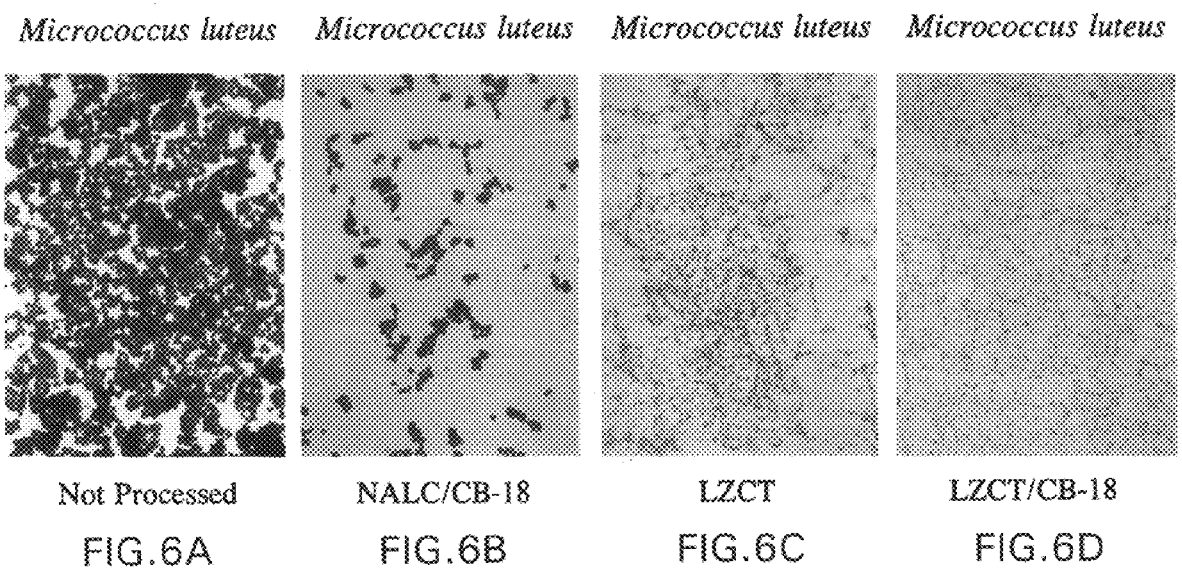

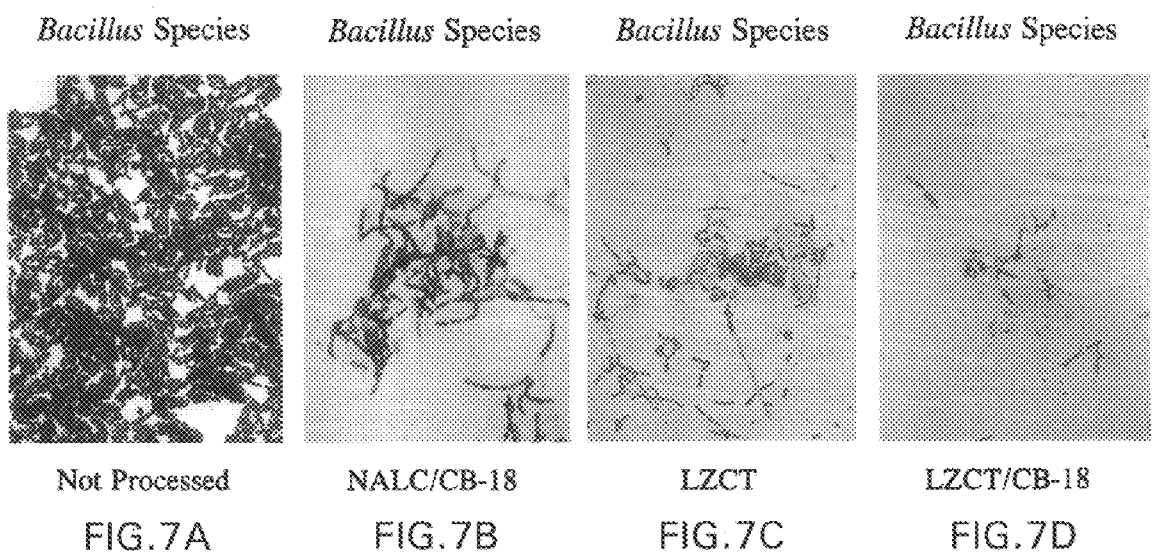
FIG.7A Not Processed — Bacillus Species
FIG.7B NALC/CB-18 — Bacillus Species
FIG.7C LZCT — Bacillus Species
FIG.7D LZCT/CB-18 — Bacillus Species

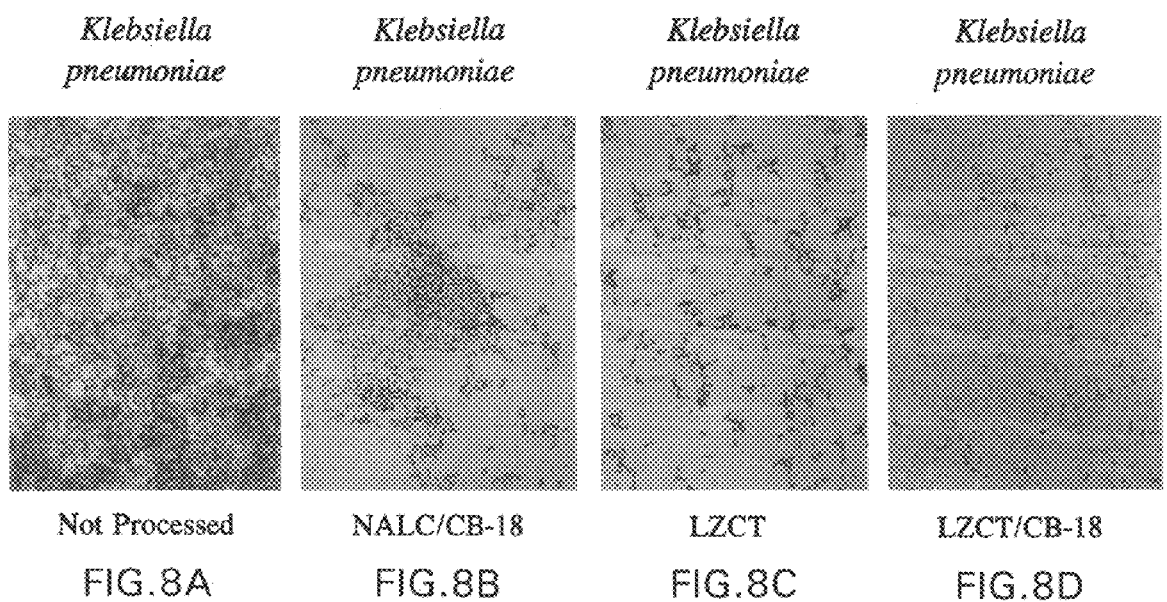

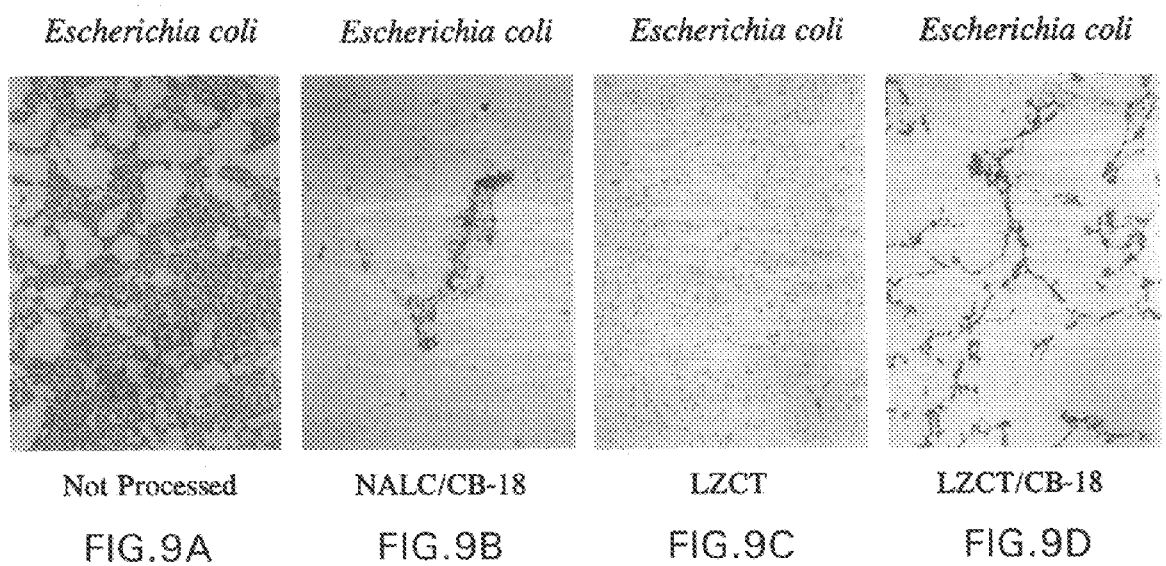
FIG.9A Not Processed — Escherichia coli
FIG.9B NALC/CB-18 — Escherichia coli
FIG.9C LZCT — Escherichia coli
FIG.9D LZCT/CB-18 — Escherichia coli Clinical Specimen: *Candida* Species

NALC/CB-18

Clinical Specimen: *Candida* Species

LZCT/CB-18

Clinical Specimen: Multiple Contaminants

NALC/CB-18

Clinical Specimen: Multiple Contaminants

LZCT/CB-18

Reverse Procedure: *Candida* Species

Reverse Procedure: *Candida* Species

Reverse Procedure: *Candida* Species

NALC/CB-18

LZCT→ CB-18

CB-18 → LZCT

Reverse Procedure: *Bacillus* Species

NALC/CB-18

Reverse Procedure: *Bacillus* Species

LZCT → CB-18

Reverse Procedure: *Bacillus* Species

CB-18 → LZCT

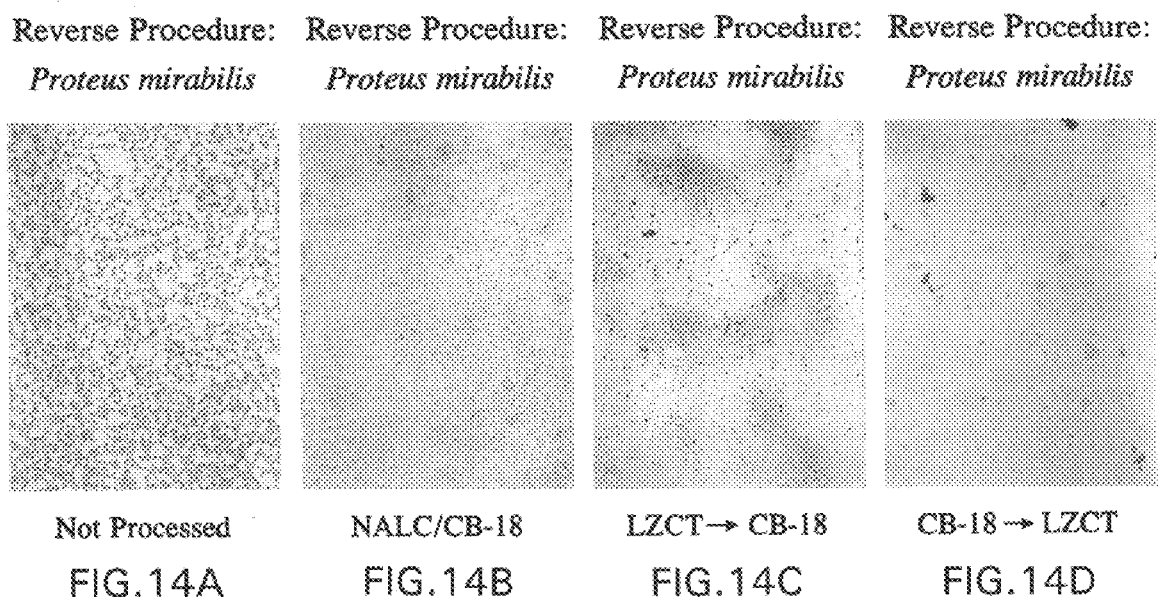

COMPOSITIONS AND METHODS FOR ENZYMATIC DECONTAMINATION

CROSS-REFERENCE TO RELATED APPLICATIONS

This application claims the benefit of U.S. Provisional Application No. 60/028,470, filed Oct. 11, 1996, the contents of which are incorporated herein by reference.

BACKGROUND OF THE INVENTION

Processing of biological and inorganic samples for the detection of mycobacteria is generally initially directed at clarification and removal of cellular or other debris, and reduction of contaminating microorganisms rather than at purification of mycobacteria per se. Thus, methods of processing biological and inorganic samples suspected of containing one or more mycobacteria, for the detection of such mycobacteria, are constrained by the presence of other, undesired microorganisms naturally present in such samples.

As one example, samples processed for mycobacterial analysis using "betaine-like" detergents as described in WO 95/27076 can still contain non-mycobacterial microorganisms in the sample at the completion of the processing. When attempts were made to culture the slow-growing mycobacteria from the processed samples, breakthrough growth of other faster-growing organisms present in the processed sample could overtake the culture, thereby causing a potential false positive result.

Such breakthrough growth is a problem as it can hinder or prevent the detection of slow-growing bacteria, and especially mycobacteria, in the sample. This problem is especially a concern for the culture of slow-growing pathogenic species of bacteria (like mycobacteria) as a patient can be misdiagnosed if the suspected microorganism cannot be cultured from that patient's samples. Hence a need exists for a method that promotes the selective recovery of a desired microorganism, especially a mycobacteria, from a s ample that may contain many other faster-growing microorganisms. Procedures designed to reduce the influence of contaminants on diagnostic utility would further improve the ability to correctly diagnose infections caused by bacteria containing mycolic acid structures, especially the diagnosis of mycobacterial infections. The invention described herein utilizes lytic enzymes as a means to purify bacteria containing mycolic acids structures for the purpose of reducing the influence of contaminants on diagnostic test results.

Noki, JP 05023167A describes a method for preparing sterile plant seedlings in which decontaminated seedlings were subjected to a vacuum. The seedlings were decontaminated by immersion into an enzyme solution that contained, inter alia, 0.1% glucanase for 2 hours at 30° C. This is stated to result in the lysis of miscellaneous germ cell walls, and the removal of fungi that are attached to the plant body surfaces. However, such treatment was an attempt to sterilize the seedlings. Recovery of any viable microorganisms from the seedling cultures after the lytic enzyme treatment was clearly undesirable.

FIELD OF THE INVENTION

The present invention is in the area of microbiological sample processing. Specifically, the present invention is directed to a composition for, and method of, enzymatic decontamination that lowers or eliminates levels of microorganisms that do not contain mycolic acid structures in their outer membranes in specimens being processed for clinical analysis. The present invention thus facilitates detection of microorganisms that contain mycolic acid structures in their outer membranes in samples that originally contained other undesired contaminating microorganisms.

SUMMARY OF THE INVENTION

In an effort to find a method for eliminating undesired organisms that are naturally associated with (i.e., naturally contaminant) biological and inorganic samples, during processing of such samples for the detection of mycobacteria, but not eliminating the mycobacteria, the inventors looked for alternatives both to the classic NaOH extraction procedure, and to the antimicrobial supplements that are commonly used in the mycobacterial art. These studies have resulted in the discovery of a method and composition for the enzymatic decontamination of extracts of biological and inorganic samples. The composition and method of the invention selectively lowers or eliminates levels of microorganisms in the sample that do not contain mycolic acid structures in their outer membranes, relative to the level of microorganisms in the sample that do contain mycolic acid structures in their outer membrane. The method of the invention utilizes one or more lytic enzymes to compromise the viability or structural integrity of contaminating microorganisms, especially non-gram negative microorganisms, in the sample. The composition and method of the invention can be used without or in addition to other agents to facilitate this end, including supplements with one or more antibiotics. Examples of antibiotic supplements that can be added include supplements directed to reducing gram negative micoorganisms, gram positive microorganisms, yeast or fungi in the sample. The composition and method of the invention significantly diminishes the number of, or eliminates completely, undesired microorganisms while retaining the viability of microorganisms that contain mycolic acid like structures in their outer membranes. This composition and method is especially useful for the processing of samples for the detection of mycobacteria.

BRIEF DESCRIPTION OF THE FIGURES

FIG. 1(A, B, C, D) is a series of photomicrographs that show the contaminant results obtained using different processing conditions and a Candida species as a prototype yeast contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 2(A, B, C, D) is a series of photomicrographs that show the contaminant results obtained using different processing conditions and a "soil saprophyte" as a prototype mold (e.g., fungi) contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 3(A, B, C, D) is a series of photomicrographs that show the contaminant results obtained using different processing conditions and an Aspergillus species as a prototype fungi (e.g., mold) contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 5(A, B, C, D) is a series of photomicrographs that show the contaminant results obtained using different processing conditions and a *Staphylococcus epidermidis* strain as a prototype gram positive cocci contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 6(A, B, C, D) is a series of photomicrographs that show the contaminant results obtained using different processing conditions and a *Micrococcus luteus* isolate as a prototype gram positive contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 7(A, B, C, D) is a series of photomicrographs that show the contaminant results obtained using different processing conditions and a Bacillus species as a prototype gram positive rod contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 8(A, B, C, D) is a series of photomicrographs that show the contaminant results obtained using different processing conditions and a *Klebsiella pneumoniae* isolate as a prototype gram negative rod contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 9(A, B, C, D) is a series of photomicrographs that show the contaminant results obtained using different processing conditions and an *Escherichia coli* strain as a prototype gram negative contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).

FIG. 14(A, B, C, D) is a series of photomicrographs that show the contaminant results obtained using different processing conditions and a *Proteus mirabilis* strain as a prototype gram negative rod contaminant. These conditions include unprocessed cells (A); cells treated with CB-18 as described in Example 1 (B); cells treated with the LZCT lytic enzyme formulation, and then with CB-18 as described in Example 6 (C); and cells treated first with CB-18 and then with LZCT as described in Example 8 (D).

DETAILED DESCRIPTION OF THE PREFERRED EMBODIMENTS

Figure 4A:
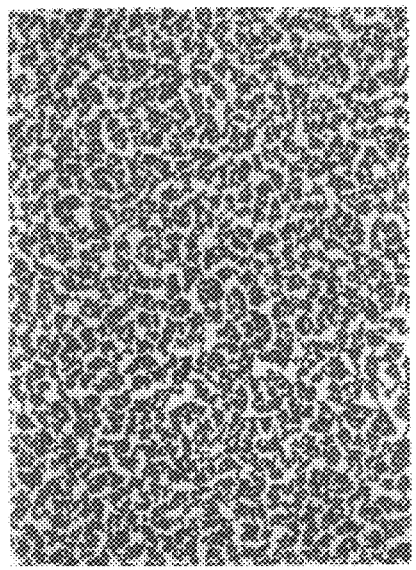
FIG. 4(A, B, C, D) is a series of photomicrographs that show the contaminant results obtained using different processing conditions and a *Staphylococcus aureus* isolate as a prototype gram positive cocci contaminant. These conditions include unprocessed cells (A); cells treated with CB-18 as described in Example 1 (B); cells treated only with the LZCT lytic enzyme formulation described in Example 5 (C); and cells treated first with LZCT and then CB-18 as described in Example 6 (D).
Figure 4B:
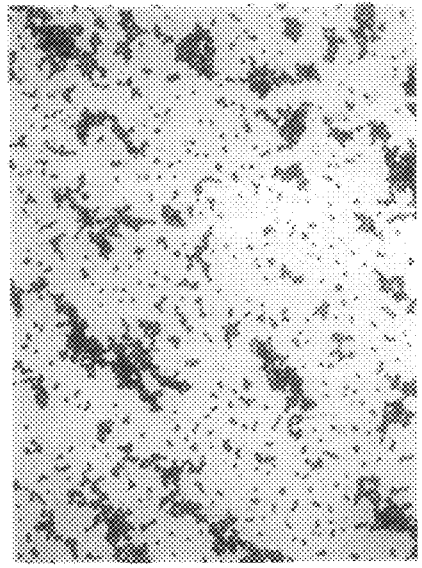
Figure 4C:
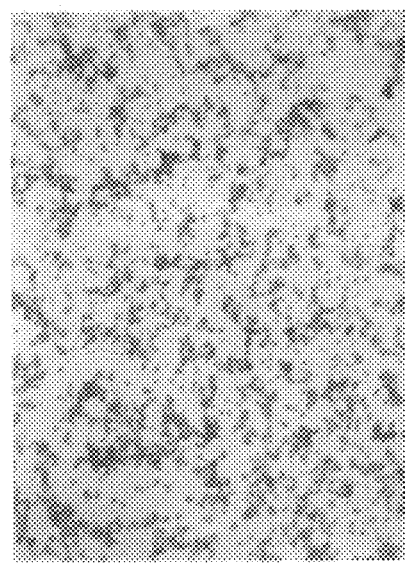
Figure 4D:
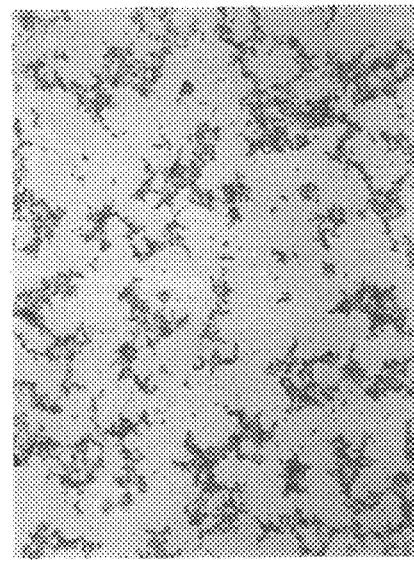

In the description that follows, a number of terms used in the chemical arts and in microbiological processing are extensively utilized. In order to provide a clear and consistent understanding of the specification and claims, including the scope to be given such terms, the following definitions are provided.

The term "betaine-like" is synonymous with "SB-18-like" as used in WO 95/27076, incorporated herein by reference. Betaine-like detergents according to WO 95/27076 have the ability to disperse cords (and clumps) of mycobacteria and/or compensate buoyancy of the mycobacteria. Dispersion of mycobacteria that cord, such as, for example, *Mycobacterium tuberculosis* complex (MTB) organisms, facilitates detection by increasing the probability that aliquots taken for detection be representative of all the types of microorganisms truly present in the whole sample. Betaine-like detergents that disperse cords have an alkyl chain length that is greater than 16 carbon atoms, and alkyl chains with 18–20 carbon atoms are most preferred.

Betaine-like detergents also have the ability to facilitate collection of mycobacteria, such as, for example, *Mycobacterium avium* complex (MAC) organisms, that do not grow in clumps, by compensating, to some degree, the natural buoyancy of such organisms. Such compensation preferably occurs by a mechanism that involves movement of the detergent into the bacterial cell. Betaine-like detergents that compensate buoyancy preferably have an alkyl chain length greater than 12 carbon atoms, and most preferably 16–20 carbon atoms.

Therefore, "betaine-like," as used herein includes structures as described in Tables 2 and 3 of WO 95/27076, and U.S. Pat. No. 5,658,749, both incorporated herein by reference, including, for example, the CB-like, SB-like, HSB-like, PB-like, StB-like, PhB-like, SoB-like, RevB-like, AO-like, cAB-like, and ImB-like compounds that possess SB-18-like activity, as described in WO 95/27076 and in U.S. Pat. No. 5,658,749.

By "betaine-like" is meant a zwitterionic compound of the structure shown in Table 1.

carboxypropyl) ammonium inner salt, or $C_{18}$-carboxypropylbetaine. CB-18 has been assigned the CAS® No. 78195-27-4.

By "SB-18" is meant N-octadecyl-N,N-dimethyl-3-ammonio-1-propane-sulfonate (CAS® No. 13177-41-8).

By "SB-16" is meant N-hexadecyl-N,N-dimethyl-3-ammonio-1-propane-sulfonate (CAS® No. 2281-11-0).

TABLE 1

The Structure of Alkyl Betaines
The general structure of n-alkyl betaines is shown. $R_1$ is the hydrophobic alkyl chain, and α is the "linkage" connecting $R_1$ to the cation, β.
$R_2$ and $R_3$ modify the cation, when required. $R_4$ is the "bridge" that connects the cation to the anion, γ.

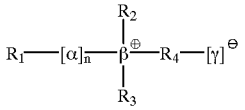

| | |
|---|---|
| $R_1$ | $C_8$–$C_{22}$ |
| α | —$CH_2$—, —CH(OH)—, —(CO)—NH—$CH_2CH_2CH_2$—, —O—, —C(O)— |
| n | 0 or 1 |
| β | —$N^{\oplus}$—, —$P^{\oplus}$—, —$S^{\oplus}$— |
| $R_2$ | —H, —$CH_3$, —$C_2H_5$, —$C_3H_7$, —$C_4H_9$ |
| $R_3$ | —H, —$CH_3$, —$C_2H_5$, —$C_3H_7$, —$C_4H_9$ |
| $R_4$ | —$CH_2$—, —$C_2H_4$—, $C_3H_6$—, —$C_4H_8$—, —$C_5H_{10}$—, —$C_6H_{12}$—, —$CH_2$—$C_6H_4$—, —$C_mH_{2m}$—, —CH(OH)$CH_2CH_2$—, —$CH_2$CH(OH)$CH_2$—, —$C_mH_{2m-1}$(OH)—; where m ≥ 1 |
| γ | —$SO_3^{\ominus}$, —$OSO_3^{\ominus}$, —$COO^{\ominus}$, —$OPO_3^{\ominus}$, —$PO_3^{\ominus}$, —$PO_2^{\ominus}$— |

By "CB-like" is meant those betaine-like detergents having a carboxylate (—$COO^{\ominus}$) moiety as the anion (e.g., carboxybetaine-like). By "SB-like" is meant those betaine-like detergents having a sulfonate (—$SO_3^{\ominus}$) moiety as the anion (e.g., sulfobetaine-like). By "HSB-like" is meant those betaine-like detergents having a sulfonate moiety as the anion, and a hydroxyl group (—OH) in the bridge (e.g., hydroxysulfobetaine-like). By "PB-like" is meant those betaine-like detergents having either a phosphate (—$OPO_3^{\ominus}$), phosphonate (—$PO_3^{\ominus}$), or a phosphinate (—$PO_2^{\ominus}$) moiety as the anion (e.g., phosphobetaine-like). By "StB-like" is meant those betaine-like detergents having a sulfate (—$OSO_3^{\ominus}$) moiety as the anion (e.g., sulfatobetaine-like). By "AO-like" is meant those betaine-like detergents having an oxide radical (—$O^{\ominus}$) as the anion (e.g., amine oxide-like). By "PhB-like" is meant those betaine-like detergents having a phosphonium (—$P^{\oplus}$—) moiety as the cation (e.g., phosphoniumbetaine-like). By "SoB-like" is meant those betaine-like detergents having a sulphonium (—$S^{\oplus}$—) moiety as the cation (e.g., sulphoniumbetaine-like). By "n-alkyl betaine" is meant those betaine-like detergents having an ammonium (—$N^{\oplus}$—) moiety as the cation (e.g., n-alkyl betaine-like). By "ImB-like" is meant those betaine-like detergents having a imidazolinium moiety as the cation (e.g., imidazoliniumbetaine-like). By "RevB-like" is meant those betaine-like detergents wherein the alkyl chain is covalently attached to the anion, as opposed to the cation (e.g., reverse betaine-like). By "cAB-like" is meant those betaine-like detergents wherein the alkyl chain is covalently attached to the bridge, as opposed to either the cation or the anion (e.g., c-alkyl betaine-like).

By "CB-18" is meant N-(3-carboxypropyl)-N,N-dimethyl-1-octadecanaminium, inner salt. CB-18 is also known as N,N-dimethyl-N-(n-octadecyl)-N-(3-

By "SB-14" is meant N-tetradecyl-N,N-dimethyl-3-ammonio-1-propane-sulfonate (CAS® No. 14933-09-6), and by "SB-12" is meant N-dodecyldecyl-N,N-dimethyl-3-ammonio-1-propane-sulfonate (CAS® No.14933-08-5).

By "mycolic acid structures" is meant chemical compounds that can be described as a β-hydroxy acid substituted at the α-position with a moderately long aliphatic chain, as understood in the art (Goren, M. B. *Bact. Rev.* 36:33–64 (1966), incorporated herein by reference). The term is synonymous with "mycolic acid-like structures." Mycolic acid structures are also collectively termed "mycolic acids." Additional tables of representative mycolic acid structures, including some that are unsaturated, cyclopropanoid, methoxylated and ketonic acids, may also be found, for example, in Lederer, E. *Chem. Phys, Lipids* 1:294–315 (1967); Lederer, E. *Pure Appl. Chem.* 25:135–165 (1971), both incorporated herein by reference. Mycolic acid structures are acid-stable molecules. Examples of classes of microorganisms that contain mycolic acid structures in their outer membranes include Mycobacterium, Nocardia, Corynebacterium, and Rhodococcus, as understood in the art.

By "contaminant," as used in the method of the invention, is meant a living microorganism, for example, a bacterium, a fungus or mold, or yeast, as understood in the art (*Manual of Clinical Microbiology* 6th Edition, Murray, P. R. et al., eds. ASM Press, Washington, D.C. (1995), incorporated herein by reference), that is present in a preparation and is other than a desired microorganism that contains mycolic acid structures in its outer membrane.

By "lytic enzyme" is meant an enzyme, as understood in the art, that has enzymatic activity against the components of the outer membrane, cell wall, capsid or capsular structures of contaminating microorganisms. That is to say that at least one substrate of such lytic enzymes is a component of the outer membrane of the contaminants (as defined above). Lytic enzymes have "lytic activity."

By "outer membrane" of a contaminant is meant the outer membrane, cell wall, capsid or capsular structures of the contaminant.

By "specimen" is meant a material from which a sample can be obtained for a desired analysis. Specimens include, but are not be limited to, biological samples and inorganic samples.

By "biological sample" is meant a sample derived from, or taken from, a specimen of biological origin, such as a specimen taken from an animal (including human) or plant. Biological samples can be derived from, or taken from any part of the biological organism, including but are not limited to expectorated matter (for example, sputum, saliva and phlegm), bronchial lavages and analogous respiratory washings, feces, tissue samples including skin samples, gastric aspirates, urine, tears, perspiration, blood and cerebral spinal fluid (CFS). Any animal species may be used as a source for such samples, including but not limited to ruminant animals (such as members of the bovine family (cattle, cows, etc.) or members of the ovine family (sheep, etc.)), pigs, fish and members of the avian family. The term biological sample is also intended to include a specimen taken from a processed or an unprocessed food source. Such processed or unprocessed food sources include, for example, a specimen derived from meat, diary products (especially, for example, eggs, cheese and milk), plants and processed food derived from plants. The term biological sample is also intended to include specimens taken from a cell culture source (such as monocyte or fibroblast cultures).

By "inorganic sample" is meant a sample derived from, or taken from, a non-biological specimen, such as, for example, from an environmental source such as soil, mud, sludge, water, sawdust and air.

By "treating" a specimen or extract thereof with a lytic enzyme is meant that the specimen or extract thereof is mixed with or otherwise in contact with such lytic enzyme under conditions in which the lytic enzyme is enzymatically active.

By a sample that is "derived from" a specimen or extract thereof is mean a sample that is directly taken from or otherwise indirectly prepared from such specimen or extract thereof through a series of procedural steps.

By "antibiotic" is meant a compound that has a deleterious effect on the viability, integrity, or competence of a contaminant, as understood in the art (see: Murray, P. R. et al., eds. *Manual of Clinical Microbiology*, ASM Press, Washington, D.C. (1995) pp.1281–1307, 1385–1404, and 1405–1414; Kucers, A. et al., *The Use of Antibiotics* $4^{th}$ ed. J. B. Lippincott Co. Philadelphia, Pa. (1987); and Lorian, V. ed. *Antibiotics in Laboratory Medicine* $2^{nd}$ Edition, Williams & Wilkins, Baltimore, Md., all incorporated herein by reference). Examples of the different classes of antibiotics include the β-lactam antibiotics, the β-lactamase inhibitors, the aminoglycosides and aminocyclitols, the quinolones, tetracyclines, macrolides, and lincosamides, as well as the glycopeptides, lipopeptides and polypeptides, the sulfonamides and trimethoprim, chloramphenicol, isoniazid, nitroimidazoles, rifampins, nitrofurans, methenamine, and mupirocin. Other antifungal compounds include the polyenes, azoles, and pyrimidine synthesis inhibitors. Any or all of these antibiotics are useful in conjunction with the methods of the invention. The term antibiotic is synonymous with "antimicrobial," as used herein.

Contemporary methods for the extraction of mycobacteria from biological and inorganic samples to ascertain the presence of mycobacteria in such samples commonly utilize the NALC/NaOH method (Kubica, G. P. W. et al., *Am. Rev. Resp. Dis.* 87: 775–779 (1963); or Kent, P. T. et al., "Public Health Mycobacteriology," in *A Guide for the Level III Laboratory*, U.S. Department of Health and Human Service, Centers for Disease Control, (1985) pp. 31–46). When organisms with mycolic acid-like structures, such as mycobacteria, are processed with the NALC/NaOH method, the specimen is first mixed with an equal volume of a solution containing 2%–4% NaOH and 0.5% of the reducing agent N-acetyl-L-cysteine (NALC). The purpose of this step is to both decontaminate and liquefy the specimen (especially respiratory specimens). The NALC facilitates liquefaction of the specimen, while the NaOH kills most contaminants, but at the expense of mycobacterial viability. The specimen is then subjected to centrifugation and the resulting sediment (e.g., pellet or "button") is used as the source of the sample that is to be assayed for the presence of the desired microorganism that contains mycolic acid structures.

Preliminary experiments that examined breakthrough contaminants from liquid culture (e.g., BACTEC 12B containing the antibiotic supplement PANTA (12B/PANTA)) of specimens that had been processed CB-18 (CB-18/12B/PANTA) revealed that there was a high incidence of gram negative rods among the contaminants (Example 1: Table 3). This was consistent with the data of Tsubone et al., *Jour. Phar. Sci.* 80:441–444 (1991) and Voss et al. *Jour. Gen. Microbiol.* 48:391–400 (1967) that showed that the betaines have a high degree of bactericidal activity against gram positive bacteria relative to such activity against gram negative bacteria.

Initially, fortifying PANTA with additional antimicrobials appeared to be the best choice to control such gram negative rod contaminants. Preliminary experiments examining the effect of different cephalosporins on mycobacterial viability suggested that ceftazidime (caz) was the best option to control contamination as it did not appear to affect the overall survival of various species of mycobacteria (data not shown). Therefore, ceftazidime was originally incorporated into the CB-18/12B/PANTA detection system to control contamination (this culture system is herein referred to as 12B/PANTA/caz).

Studies described herein (e.g., the CB-18 Pilot Study (Example 2)) comparing mycobacterial processing methods revealed that the contamination rate (e.g. the amount of non-mycobacterial growth in the processed population on a per specimen basis) was approximately 7.5% when samples were extracted by the NALC/NaOH method according to Kubica, G. P. W. *Am. Rev. Resp. Dis.* 87:775–779 (1963); or Kent, P. T. et al., "Public Health Mycobacteriology," in *A Guide for the Level III Laboratory*, U.S. Department of Health and Human Service, Centers for Disease Control, (1985) pp. 31–46, and analyzed by growth in liquid culture (12B/PANTA). The same group of specimens, when processed using the CB-18 method according to WO 95/27076, and planted on 12B/PANTA/caz, had a contamination rate approaching 21%. The CB-18 contamination rate was high, even in the presence of ceftazidime fortified PANTA, and additional research to control contamination was desirable.

Further studies that examined mycobacterial viability, however, revealed that the viability of some mycobacterial isolates were, in fact, compromised by the combination of PANTA/caz and CB-18, but only when the CB-18 concentration was between 15–35 μg/ml in the culture media during incubation. This was initially revealed in the sensitivity of liquid culture. For example, the detection of mycobacteria in the CB-18/12B/PANTA/caz culture system was dramatically decreased (Example 4: Table 6). Table 6 showed that the NALC/NaOH culture sensitivities of liquid and solid media were 98.4% and 75.4%, respectively. The sensitivities of liquid and solid media for CB-18 in this study were 64.0% and 83.1%, respectively. While the liquid media of all NALC/NaOH processed specimens contained an antibiotic supplement as discussed above (e.g., PANTA), the higher sensitivity of the liquid media was the expected result. Table 6 showed that the CB-18 liquid culture sensitivity was depressed even though CB-18 provided a 46% increase in overall culture sensitivity. While the combination of CB-18 and antibiotics was responsible for this loss in liquid culture sensitivity, the fortification of PANTA with caz appeared to exacerbate this loss. Therefore, the addition of more caz, or of antibiotics in general, for the purpose of controlling breakthrough growth of undesired organisms, was not an effective solution due to the complexity of the problem.

Identification of contaminants isolated during the CB-18 Pilot Study (Example 2: Table 4), showed a rather remarkable dichotomy relative to the earlier results (Example 1: Table 3). For example, while the respective contamination rates were 20.8% (Table 4) and 14.4% (Table 3), the results presented in Table 3 revealed that 84% of the identified contaminants were gram negative bacteria, whereas only 38% of the contaminants isolated in the CB-18 Pilot Study (Table 4) were gram negative bacteria. The difference between these two groups of specimens was that the former (Table 3) were collected from among respiratory specimens submitted for routine work to the microbiology laboratory at Quest Diagnostics, Incorporated (QDI) in Baltimore, Md., and the latter (Table 4) were derived exclusively from specimens submitted to five tuberculosis (TB) laboratories that participated in the CB-18 Pilot Study described herein. Scrutiny of the QDI-Baltimore contaminants in the CB-18 Pilot Study (Example 3: Table 5) revealed that they were consistent with the general trend of all specimens in the study, suggesting that the differences between these two groups of clinical specimens was legitimate. These studies revealed, for the first time, that the focus of efforts to control breakthrough contamination in a desired sample being assayed for the presence of microorganisms containing mycolic acid structures needed to be changed from the art-directed focus that primarily attempted to control gram negative contamination (such as that shown in Table 3) through the addition of antibiotics, to a focus that primarily controls contaminants by eliminating gram positive and mycologic contaminants (e.g., yeasts and molds), (the contaminant spectrum shown in Table 4), alone or in addition to control of gram negative contamination.

According to the invention, undesired microorganisms, especially non-gram negative microorganisms, are eliminated or reduced in samples by treating S the sample with one or more lytic enzymes. The lytic enzyme treatment preferably selectively degrades or weakens the integrity of the cell walls of the contaminants to a degree sufficient to lessen the structural integrity, viability or growth of the same, thus facilitating the detection of microorganisms that contain mycolic acid structures in their outer membranes from the sample after the lytic enzyme treatment. According to the invention, a method and composition are provided for the decontamination of biological and inorganic samples, especially samples processed by methods likely to lead to the breakthrough growth of such contaminants, especially non-gram negative contaminants, by the addition of one or more lytic enzymes and/or agents that stimulate the activity of such enzymes. The treatment with lytic enzymes can occur before, during or after the sediment preparation, or at more than one of those stages (with the same or with different enzymes), or continuously through the preparation.

Thus, in a first embodiment, the sample is treated with a composition containing one or more desired lytic enzyme(s) prior to any processing step. This embodiment is especially useful for liquid samples that require no homogenization or solubilization, such as water. Air samples can be bubbled through such a lytic enzyme-containing composition, or a filter onto which microbes present in the air have been trapped can be directly added to the lytic enzyme containing-composition. This embodiment is also useful for the treatment of solid samples to effect a preliminary decontamination of the contaminated exterior of the sample. The lytic enzyme composition need not be removed prior to homogenization or dissolution of a solid sample, and it is not necessary to inactivate the lytic enzyme activity prior to subsequent processing steps. Lytic enzymes added at any stage in preparation may be active both at that stage in processing and, if desired, at subsequent stages of the processing. The lytic enzyme treatment can, if desired, be provided prior to subsequent handling of the specimen or sample, for example, in the field or location at which the specimen or sample is first taken, and the specimen or sample then frozen or otherwise stabilized against decomposition until further processing is desired or can be performed. Alternatively, the container into which the sample is placed can be coated with or otherwise contain a desired lytic enzyme composition. For example, blood samples can be drawn into tubes that contain the appropriate amounts of one or more desired lytic enzymes. Transport of samples, especially solid samples, in a solution containing the lytic enzyme compositions of the invention, is especially useful to protect against further contamination of the sample or against the growth of endogenous contaminants already present on the sample.

In a preferred embodiment, a lytic enzyme treatment is provided during the initial processing of the sample; the initial processing generally effects dissolution or homogenization of particulate matter of which the sample is composed. Lytic enzymes can be added directly to the solution in which the sample is processed, for example, the homogenization or solubilization or lyophylization solution, and remain active (or at least not be specifically inactivated) during such homogenization, solubilization or lyophylization. The enzymes can also be active subsequent to such steps. This embodiment is especially useful when it is desired to process a solid specimen as soon as possible, without letting the solid form sit for a prolonged time. As exemplified using the CB-18 procedure shown in Example 1, an appropriate step at which to add the lytic enzymes in this embodiment is in the NALC liquefaction step (Example 1: Step 2). The lytic enzymes can be premixed with the NALC solution. The NALC solution thus provides a buffered cocktail containing the appropriate lytic enzymes.

In a second preferred embodiment, a lytic enzyme treatment is provided at one or more steps subsequent to the initial processing step. This may be in lieu of a treatment earlier in the processing, or in addition to an earlier treatment. Assuming that this treatment is in addition to a previous treatment, the composition of the lytic enzyme solution may be the same as or different than a previous solution, as desired. As exemplified using the CB-18 procedure of Example 1, the lytic enzymes are added at a step wherein the sediment is re-suspended (as in Example 1: Step 10). It is also possible to add such enzymes to the re-suspension solution so as to provide in the re-suspension solution a buffered cocktail containing the appropriate lytic enzymes.

In a third preferred embodiment the culture media itself, into which the sample of the sediment is cultured, contains the desired lytic enzyme(s). In this embodiment, it is preferable that the enzymes be active during the initial stage of culture. The lytic enzyme solution can be added directly to the culture bottle or provided with the medium. In one example of the third preferred embodiment, the specimen is first processed with a betaine-like detergent, re-suspended in water or buffer and then added to the culture media immediately before, or immediately following, addition of the lytic enzymes to the culture media. If desired, treatment with the lytic enzyme solution during culture may be in addition to treatment with lytic enzymes earlier in the processing stage. However, adding the lytic enzyme solution to the culture is more expensive and less efficient than the other embodiments due to the restrictions imposed by the culture media itself. For example, the culture medium would be required to be optimal for growth of bacteria containing mycolic acid structures (e.g., pH, ionic strength, etc.), rather than being designed for the enzymatic activity of the lytic enzymes.

None of the embodiments described above is intended to be exclusive to the other. That is, the desired lytic enzyme can be added to the preparation in a protocol that encompasses one or more of the examples discussed above.

The lytic enzymes can be in a solubilized form, or a solid form, or otherwise attached to a solid support, such as, for example, a bead. Providing the lytic enzyme in bead form allows the easy extraction of most or all of the lytic enzymatic activity from the sample, by simply removing the beads from the sample. Alternatively, the lytic enzymes can be bound to a solid support, such as the interior of a column, test tube or carrier, against which the sample comes into contact.

One or more different lytic enzymes may be present in the composition, and the choice of which lytic enzyme(s) to use will generally depend upon the type of contaminants it is desired to eliminate or lessen. A group of different lytic enzymes can be used, separately or together, to decontaminate the sample of one species of contaminant. Alternatively, a group of different lytic enzymes can be used, separately or together, to decontaminate the sample of more than one species of contaminants. When different lytic enzymes are used, and when it is desired to treat the sample with different lytic enzymes in a defined order, such that one or more enzymes are present alone or are otherwise at reduced levels when exposed to the other lytic enzymes, then providing such enzymes attached to a solid structure facilitates the removal of each lytic enzyme so that the next one in the order can be added.

Thus, according to the methods of the invention, a processing step such as the exemplified NALC liquefaction step, or the exemplified re-suspension step, also becomes an enzymatic decontamination step in which the integrity of the undesired microorganisms is compromised. The integrity of the undesired microorganism is preferably compromised by reducing their viability, lysing them or by destabilizing their structural integrity, directly as a result of the exposure to the lytic enzymes. Additionally, the integrity of the undesired microorganism can be compromised indirectly, as a result of the lytic enzyme treatment, making such contaminants more susceptible to the germicidal or surface active effects of betaine-like detergents (e.g., CB-18) and/or antibiotics. Similar to processing with betaine-like detergents, when it is desired to add one or more antibiotics to the preparation, exposure of the contaminants to antibiotics can take place before, during or after exposure to the lytic enzymes. Incorporation of PANTA into the 12B culture system is one example wherein exposure to antibiotics is provided following lytic enzyme treatment.

When using a method other than the NALC method, such as the methods that utilize a betaine-like detergent according to WO 95/27076, a similar strategy to that above can be used. In addition, the specimen can be subjected to enzymatic decontamination either before treatment with the betaine-like detergent, during treatment with the betaine-like detergent, or following processing with the betaine-like detergent.

Thus, in a first preferred embodiment when using a betaine-like detergent, an enzymatic decontamination step can be performed prior to treatment with the betaine-like detergent. In a second preferred embodiment when using a betaine-like detergent, an enzymatic decontamination step is included during the treatment with the betaine-like detergent. In a third preferred embodiment when using a betaine-like detergent, an enzymatic decontamination step is included following treatment with the betaine-like detergent. As above, more than one enzymatic decontamination steps can be performed, encompassing one or more of the above embodiments, or, the enzymatic decontamination step can be continuous throughout the processing. In any of these embodiments, inclusion of a reducing agent such as NALC, or a separate step incorporating a reducing agent, is not essential, but preferred, especially with respiratory specimens due to NALC's ability to deliquesce sputum.

If a liquefaction step is included then decontamination with the lytic enzyme solution can occur either simultaneously with or independent of the NALC liquefaction step, and before processing with the betaine-like detergent. Alternatively, enzymatic decontamination can be independent of, and/or follow, both the NALC liquefaction step and treatment with a betaine-like detergent.

Other reducing agents are useful in conjunction with the methods of the invention if they act in a manner similar to NALC. Examples of such reducing agents include, but are not limited to, dithiothreitol (DTT) and β-mercaptoethanol (β-ME).

In general the first preferred embodiments described above are most efficient when the primary method of detection is by either culture or amplification. For example, the first preferred embodiment as exemplified in Example 5 minimizes the number of manipulations required to prepare the specimen for detection. In general, the second preferred embodiment (as exemplified in Example 7) is most efficient when the primary method of detection is by amplification, but culture methods are also employed for specimens positive by amplification. For example, many diagnostic algorithms designed solely for use in conjunction with amplification may not necessarily require enzymatic decontamination (e.g., the advantages of enzymatic decontamination in relation to amplification are accrued only in extreme cases, fecal specimens for example). Alternatively, decontamination prior to analysis by culture is improved for almost all specimen types. In those instances where both methods are used, and amplification precedes culture, the second preferred embodiment minimizes the expense associated with enzymatic decontamination by subjecting only positive specimens to treatment with the enzyme cocktail.

However, the second preferred embodiment is especially desired for another reason. For example, some specimen types require clarification and are also heavily populated by contaminants; such as respiratory, fecal or soil specimens. Processing such specimens may even require a clarification step prior to treatment with betaine-like detergents. Excessive contaminants would all but preclude culture as a means of detection, and high concentrations of heterologous nucleic acids, nucleases, and proteases associated with such specimens would affect the efficiency of amplification or immunodiagnostics. Example 8 exemplifies that the second preferred embodiment described in Example 7, wherein the specimen is pre-treated with a betaine-like detergent (e.g., CB-18) prior to exposure to the lytic enzyme cocktail. The embodiment of Example 7 is generally more efficient at destabilizing the structural integrity of contaminants. In addition to the concept that the integrity of the specimen is relieved (e.g., liquified), the peripherally associated components associated with many contaminants (e.g., proteins, lipids, lipoproteins, lipopolysaccharides, and other complex polysaccharides), can be stripped to some degree by first treating the specimens with a betaine-like detergent. Exposed structural components are more easily digested with lytic enzymes. Therefore, the second preferred embodiment is generally more efficient at decontaminating clinical specimens for culture, and helps reduce the complexity of the sediment for nucleic acid amplification or immunodiagnostics.

Lytic Enymes

The components of the outer membrane are typically composed of a complex array of carbohydrate, lipid and amino acid constituents as understood in the art (Joklik, W. et al., eds. *Zinsser Microbiology* $17^{th}$ Edition, Appleton-Century-Crofts, New York. (1980) pp.106–134 and 1326–1337). These constituents can be covalently linked to form polymeric regions of a given component (e.g., polysaccharides or polypeptides), or linked to each other to form heterogeneous matrixes (e.g., lipopolysaccharides, lipoproteins, or carbohydrate/polysaccharide-modified amino acids/polypeptides (i.e., amino sugars)). For example, carbohydrate constituents are commonly known as glycosides, and polymerized carbohydrates form polysaccharides, also known as glycans (Lehninger, A. L. *Biochemistry* $2^{nd}$ Edition, Worth Publishers, Inc., New York (1975) pp.249–277). In bacteria the primary structural feature of this complex array within the outer membrane is the peptidoglycan, or murein, as understood in the art.

The function of lytic enzyme(s) in the methods of the invention is to enzymatically cleave covalent bonds between cellular components and/or constituents (such as those described above) that are substrates for such enzymes. When these bonds are cleaved, the structural integrity of the contaminant is compromised. The covalent bonds to be cleaved can be within homopolymeric regions (e.g., within polysaccharides or polypeptides), or at the junction between different components (e.g., within amino acid sugars; between carbohydrates and lipids; and between amino acids and lipids). Enzymes that cleave these bonds are commonly known as "hydrolases" as used herein. There are a wide variety of lytic enzymes that cleave glycosidic bonds, polysaccharides or glycan strands (e.g., glycosidases, polyaccharases and glycanases, respectively). Peptide hydrolases cleave polypeptides between amino acids. Peptide hydrolase is synonymous with peptidase protease, or proteinase as used herein. Examples of classes of hydrolases useful in the methods of the invention, as hereinafter defined, would include agarases, aminidases, amidases, arabinosidases, cellulases, chitinases, dextranases, dextrinases, fructofuranosidases, fructosidases, fucoidanases, fucosidases, furanosidases, galactanases, galactosidases, galacturonases, galacturonosidases, glucanases, glucosidases, glucanohydrolases, glucohydrolases, glucuronidases, glycanases, glycosidases, laminarinases, lichenases, mannanases, mannosidases, pectinases, peptidases, polysaccbarases, proteases, proteinases, pullanases, rhamnosidases, trehalases, xylanases, and xylosidases.

Enzymatic activity can be classified based on the reaction catalyzed, or the structure of the substrate. Cleavage can occur between constituents within the homopolymeric regions (e.g., the "endo-" activity), or at the termini of said regions (e.g., the "exo-" activity). Any of these enzymes that are specified as having the so called "endo-" or "exo-" activity, or both, or lytic enzymes that are similar in enzymatic function to the enzymes listed above (but not having the exact name stated above, and instead are named according to structural or conformational modifications of the substrate), are considered as being embodied within this list, and are, therefore, considered as being useful in the methods of the invention. Generally speaking, the exact name of an enzyme specifies both the substrate and the catalytic reaction. The important aspect of lytic activity is not so much the exact name, reaction or classification of the enzyme, but its function in the methods of the invention; specifically the ability of such lytic activity to destabilize the structural integrity of said contaminant in the methods of the invention. For example, since the outer membrane is an essential aspect of structural integrity and/or viability of the contaminant, destabilizing the outer membrane matrices lessens the ability of the contaminants to remain physically intact, and/or to continue to survive (e.g., maintain viability). The unique aspect of the invention herein is that such lytic activity does not affect the structural integrity of bacteria containing mycolic acid structures, but instead is specific for the outer membrane components of contaminating microorganisms in the specimen.

Lytic enzymes dismantle the matrices that form the structural framework (i.e., the outer membrane) surrounding said contaminants by cleaving the covalent bonds interlinking the components of said outer membrane. Degradation of the outer membrane, therefore, can require a diverse array of enzymatic activities. There are several categories of lytic activities that are especially useful in the methods of the invention. These would include enzymes active on macromolecules that contain polymerized amino acids (e.g., peptides or proteins), and/or polymerized carbohydrates (polysaccharides or glycans), as well as enzymes that are specific for the covalent bonds that link carbohydrates and amino acids (e.g., amino sugars). These enzymes are generally known as hydrolases (Dixon, M. et al., *Enzymes* $3^{rd}$ *Edition*, Academic Press, New York, (1979) pp.300–316 (incorporated herein by reference)).

Hydrolases active on polymerized amino acids (peptide hydrolases), more commonly known as proteases, peptidases, or proteinases are cataloged according to enzyme nomenclature as understood in the art (Commission on Biochemical Nomenclature, *Enzyme Nomenclature*, Elsevier Scientific Publishing Co., Amsterdam (1973) beginning at p.228 (incorporated herein by reference)) as having the first two digits of their enzyme classification numbers ("E.C.") as "3.4". For example, exopeptidases have classification numbers ranging from E.C. 3.4.11 thru E.C. 3.4.15, and proteinases have classification numbers ranging from E.C. 3.4.21 thru E.C. 3.4.24. All are useful in the methods of the invention, but are expected to be most useful in combination with hydrolases that are active on glycosyl compounds. That is to say that because peptide hydrolases cleave covalent bonds found in the outer membranes of contaminants, such hydrolyases are useful in the methods of the invention. However, due to the composition of the outer membranes of the contaminants, in the most preferred embodiments of the invention, hydrolases active on carbohydrates are preferably included in the lytic formulation.

Hydrolases having activity on carbohydrates have the first two digits of their classification numbers as "3.2" (Commission on Biochemical Nomenclature, *Enzyme Nomenclature*, Elsevier Scientific Publishing Co., Amsterdam (1973) p.212–227; Dixon, M. et al., *Enzymes 3rd Edition*, Academic Press, New York, (1979) pp.860–872; and Barman, T. E. Enzyme Handbook Vol II, Springer-Verlag, New York (1969) pp. 560–594 (all incorporated herein by reference)). Glycosidases are subdivided into groups depending the substrate. Enzymes preferred in the methods of the invention include those specific for the following linkages: O-glycosyl-(e.g., being classified as E.C. 3.2.1 enzymes), N-glycosyl-(e.g., being classified as E.C. 3.2.2 enzymes), and S-gylcosyl-(e.g., being classified as E.C. 3.2.3 enzymes). Given the outer membrane structures of these contaminants, the most preferred glycosidases are those active on O-glycosyl-linkages (e.g., E.C. 3.2.1 enzymes).

Examples of glycosidases active on O-glycosyl-linkages (e.g., E.C. 3.2.1 enzymes) include, but not be limited to, α-amylase (E.C. 3.2.1.1), β-amylase (E.C. 3.2.1.2), exo-1,4-α-D-glucosidase (E.C. 3.2.1.3), cellulase (E.C. 3.2.1.4), endo-1,3(4)-β-D-glucanase (E.C. 3.2.1.6), endo-1,4-β-D-xylanase (E.C. 3.2.1.8), oligo-1,6-glucosidase (E.C. 3.2.1.10), dextranase (E.C. 3.2.1.11), chitinase (E.C. 3.2.1.14), polygalacturonase (E.C. 3.2.1.15), lysozyme (E.C. 3.2.1.17), neuraminidase (E.C. 3.2.1.18), α-D-glucosidase (E.C. 3.2.1.20), β-D-glucosidase (E.C. 3.2.1.21), α-D-galactosidase (E.C. 3.2.1.22), β-D-galactosidase (E.C. 3.2.1.23), α-D-mannosidase (E.C. 3.2.1.24), β-D-mannosidase (E.C. 3.2.1.25), β-D-fructofuranosidase (E.C. 3.2.1.26), β-N-acetyl-D-glucosaminidase (E.C. 3.2.1.30), β-D-glucuronidase (E.C. 3.2.1.31), endo-1,3-β-D-xylanase (E.C. 3.2.1.32), amylo-1,6-glucosidase E.C. 3.2.1.33), hyaluronoglucosarninidase (E.C. 3.2.1.35), hyaluronoglucuronidase (E.C. 3.2.1.36), exo-1,4-β-D-xylosidase (E.C. 3.2.1.37), β-D-fUcosidase (E.C. 3.2.1.38), endo-1,3-β-D-glucanase (E.C. 3.2.1.39), α-L-rhamnosidase (E.C. 3.2.1.40), pullanase (E.C. 3.2.1.41), β-L-rhamnosidase (E.C. 3.2.1.43), fucoidanase (E.C. 3.2.1.44), sucrose α-D-glucohydrolase (E.C. 3.2.1.48), α-N-acetyl-D-galactosaminidase (E.C. 3.2.1.49), α-N-acetyl-D-glucosaminidase (E.C. 3.2.1.50), α-L-fUcosidase (E.C. 3.2.1.51), β-N-acetyl-D-hexosaminidase (E.C. 3.2.1.52), β-N-acetyl-D-galactosaminidase (E.C. 3.2.1.53), cyclomaltodextrinase (E.C. 3.2.1.54), α-L-arabinofuranosidase (E.C. 3.2.1.55), glucuronosyl-disulphoglucosamine glucuronidase (E.C. 3.2.1.56), isopullanase (E.C. 3.2.1.57), exo-1,3-β-D-glucosidase (E.C. 3.2.1.58), endo-1,3-α-D-glucanase (E.C. 3.2.1.59), exo-maltotetraohydrolase (E.C. 3.2.1.60), mycodextranase (E.C. 3.2.1.61), 1,2-α-L-fucosidase (E.C. 3.2.1.63), 2,6-β-D-fructan 6-levanbiohydrolase (E.C. 3.2.1.64), levanase (E.C. 3.2.1.65), quercitrinase (E.C. 3.2.1.66), exopolygalacturonase (E.C. 3.2.1.67), isoamylase (E.C. 3.2.1.68), exo-1,6-α-D-glucosidase (E.C. 3.2.1.70), endo-1,2-β-D-glucanase (E.C. 3.2.1.71), exo-1,3-β-D-xylosidase (E.C. 3.2.1.72), lichenase (E.C. 3.2.1.73), exo-1,4-β-D-glucosidase (E.C. 3.2.1.74), endo-1,6-β-D-glucanase (E.C. 3.2.1.75), exo-1,2-1,3-α-D-mannosidase (E.C. 3.2.1.77), endo-1,4-β-D-mannanase (E.C. 3.2.1.78), exo-β-D-fructosidase (E.C. 3.2.1.80), agarase (E.C. 3.2.1.81), exo-poly-α-D-galacturonosidase (E.C. 3.2.1.82), κ-carrageenanase (E.C. 3.2.1.83), exo-1,3-α-D-glucanase (E.C. 3.2.1.84), 6-phospho-β-D-galactosidase (E.C. 3.2.1.85), 6-phospho-β-D-glucosidase (E.C. 3.2.1.86), capsular-polysaccharide galactohydrolase (E.C. 3.2.1.87), β-Larabinosidase (E.C. 3.2.1.88), endo-1,4-β-D-galactanase (E.C. 3.2.1.89), endo-1,3-β-D-galactanase (E.C. 3.2.1.90), exo-cellobiohydrolase (E.C. 3.2.1.91), exo-β-N-acetylmuraminidase (E.C. 3.2.1.92), α,α-phosphotrehalase (E.C. 3.2.1.93), exo-isomaltohydrolase (E.C. 3.2.1.94), exo-isomaltotriohydrolase (E.C. 3.2.1.95),endo-β-N-acetylglucosaminidase (E.C. 3.2.1.96), endo-α-N-acetylgalactosaminidase (E.C. 3.2.1.97), exo-maltohexaohydrolase (E.C. 3.2.1.98). Enzymes not listed herein, but having the O-glycosyl-linkage as the substrate (e.g., E.C. 3.2.1 enzymes), would also be useful in the methods of the invention.

The enzymes discussed above are, therefore, summarized and defined herein as belonging to one or more of the following groups of hydrolases: agarases, aminidases, amidases, arabinosidases, cellulases, chitinases, dextranases, dextrinases, fructofuranosidases, fructosidases, fucoidanases, fucosidases, furanosidases, galactanases, galactosidases, galacturonases, galacturonosidases, glucanases, glucosidases, glucanohydrolases, glucohydrolases, glucuronidases, glycanases, glycosidases, laminarinases, lichenases, mannanases, mannosidases, pectinases, peptidases, polysaccharases, proteases, proteinases, pullanases, rhamnosidases, trehalases, xylanases, and xylosidases.

The classic example of a bacteriolytic enzyme, and one that represents the endo-β-1,4-N-acetylhexosaminidases, is lysozyme (Shugar, D., *Biochem. Biophys. Acta* 8:302–309 (1952)). Lysozyme (muraminidase or N-acetylmuramide glycanohydrolase) degrades the glycosaminoglycans (a.k.a., mucopolysaccharides) in the cell walls of all bacteria, for example by cleaving the glycan strands in the peptidoglycan. Other useful and well known lytic enzymes include cellulases, which cleave the linkages in β-D-glucans, chitinases, which cleave the 1,4-β-actetamido-2-deoxy-D-glucoside linkages in chitin, and pectinases, which cleave methyl-D-galacturonate linkages. These various forms of polymerized carbohydrates are commonly found in the cell walls of many bacterial and/or mycologic contaminants. Andrews et al., *TIBTECH* 5:273–277 (1987), incorporated herein by reference, reviews enzymatic lysis mechanisms and uses. Not intending to be limited to the following listing of enzymes, Table 2 lists examples of some of the commercially available enzymes that are most useful in the compositions and methods of the invention.

TABLE 2

Some Commercially Available Lytic Enzymes Useful in the Invention

| Source | Activities |
| --- | --- |
| Chicken egg whites (Lysozyme) | Muraminidase |
| Oerskovia xanthineolytica ("Lyticase/Zymolyase") | Endoglucanase Protease |
| Aspergillus species | Cellulase Pectinase |

TABLE 2-continued

Some Commercially Available Lytic Enzymes Useful in the Invention

| Source | Activities |
|---|---|
| *Rhizoctonia solani* | Glucanase |
| | "Cell Lytic Activity" |
| | Protease |
| *Trichoderma harzianum* | Cellulase |
| *Trichoderma reesei* | Chitinase |
| | Protease |
| Cytophaga species | Protease |
| | Amidase |
| *Achromobacter lyticus* ("Achromopeptidase") | Protease |
| *Streptomyces globisporus* 1829 ("Mutanolysin") | Protease |
| | Endo-glycosidase |
| *Staphylococcus aureus* ("Lysostaphin") | Endo-β-N-acetylglucosaminidase |
| | endopeptidase |
| | N-acetylmuramyl-L-alanine amidase |

Lysozyme (such as that sold by Sigma, St. Louis, Mo. (Cat. #: L 6876)) alone may not be sufficient for elimination of some of the undesired bacteria. Many bacteria have additional components (e.g., proteins, lipids, lipoproteins, lipopolysaccharides, and other complex polysaccharides) that protect the peptidoglycan from the action of lysozyme. However, if these components are compromised or removed, the peptidoglycan can be digested with lysozyme. For example, Cisani et al., *Antimicrob. Agents Chemo.* 21:531–535 (1982) show that the action of lysostaphin is dramatically enhanced by lysozyme. Therefore, combinations of lytic enzymes are preferred because these combinations can provide significant advantages for decontamination purposes.

Lysis of yeast can be accomplished with lyticase (such as that sold by Sigma, St. Louis, Mo. (Cat. #: L 4025), or Boehringer Mannheim, Indianapolis, Ind. (Cat. #: 1 372 467)). Lyticase is also known as zymolyase. This is actually a combination of two enzymatic activities, an endoglucanase activity and a protease activity (Scott et al., *J. Bacteriol.* 142:414–423 (1980)). Other commercially available enzyme preparations (Table 2) include extracts from Aspergillus species, *Rhizoctonia solani*, *Trichoderna harzianum*, and Cytophaga species (useful preparations from each these four species are also sold by the Sigma Chemical Company, St. Louis, Mo., Cat. #'s: L 3768, L8757, L 2265 and L 9893, respectively). These preparations have lytic activity against a variety of organisms, from bacteria and yeast, to fungi and even plants. In addition to these enzymes, other commercially available enzyme preparations useful in the methods of the invention include achromopeptidase (Ezaki, et al., *J. Clin. Micro.* 16:844–846 (1982)), mutanolysin (Calandra et al., *Infect. Immun.* 28:1033–1037 (1980)), and lysostaphin (Wadstrom et al., *Acta Path. Microbiol. Scand.* B, 79:248–264 (1971)). Achromopeptidase (such as that sold by Sigma, St. Louis, Mo., Cat. #'s: A 3422, A 7550 or A 3547), and mutanolysin (such as that sold by Sigma, St. Louis, Mo., Cat. #'s: M 9901 or M 4782) appear to be fairly specific for Streptococcus and some gram positive cocci, and lysostaphin (such as that sold by Sigma, St. Louis, Mo., Cat. #'s: L 0761, L 4402, L 7386, or L2898) digests Staphylococcus species and other gram positive rods such as such as Bacillus species.

Lytic enzyme preparations listed herein from representative species within a given genus are not intended to be limited to that species. For example, while Table 2 notes the commercial availability of lytic enzymes from specific species such as Aspergillus, Rhizoctonia, Trichodenna, Cytophaga, Achromobacter, Streptomyces, Oerskovia, and Staphylococcus, lytic enzymes derived from other species can reasonably be expected to be equivalent in the methods of the invention. Other genera known to produce lytic enzymes useful in the methods of the invention include, but are not limited to, Arthrobacter, Brevibacterium, Flavobacterium, Penicillium, Micromonospora, and Bacillus. Generally, it is to be expected that it is the lytic activity that is important rather than the species from which the lytic enzyme is derived.

Combinations of the enzymes discussed above minimize or eliminate contamination of yeast, fungi, and many gram positive organisms. However, digesting the cell wall of gram negative bacteria is a more difficult task due to its more complex structure. The envelopes of gram negative organisms are dramatically more complex. For example, the peptidoglycan is covered in a thick layer composed primarily of lipids and lipopolysaccharides (LPS). Consequently, affecting the integrity of the cell wall of gram negative bacteria is more difficult. When it is desired to attack the cell wall of gram negative bacteria, the Cytophaga protease/amidase preparation is useful. In addition, extracts from Micromonospora species (Suzuki et al., *Agric. Biol. Chem.* 49:1719–1726 (1985)) have significant activity against (compromise the integrity of) gram negative organisms. Such preparations are useful for the preparation of a cocktail to minimize or eliminate contamination of processed mycobacterial samples by gram negative bacteria. Those of skill in the art will recognize that other extracts not discussed here are available to accomplish decontamination that could reasonably be expected to enhance the methods of the invention when combined with processing with betaine-like detergents such as the processing methods taught in WO 95/27076 (e.g., CB-18 processing).

Therefore, the methods of the invention generally provide a composition that comprises one or more lytic enzymes, preferably a buffered enzyme cocktail (mixture), the enzyme or enzymes in the composition having activity against (being able to compromise the viability or integrity of) one or more non-mycobacterial organisms. Preferably, the composition possesses a broad spectrum against multiple non-mycobacterial organisms. In a preferred embodiment, the enzyme cocktail contains lysozyme or lyticase, and in a highly preferred embodiment, at least both lysozyme and lyticase. In an especially preferred embodiment, the enzyme cocktail contains lytic enzyme-containing extracts of Trichoderma and/or Cytophaga, in addition to lysozyme and/or lyticase, but most especially lytic enzyme-containing extracts of both Trichoderma and Cytophaga in addition to lysozyme and lyticase. In another especially preferred embodiment, the enzyme cocktail contains at least one lytic enzyme, or lytic enzyme-containing extract, that provide lytic enzyme activity against gram negative contaminants (for example, a lytic enzyme or lytic enzyme-containing extract of the Micromonospora species), especially in addition to lytic enzyme containing extracts from Trichodenna and Cytophaga (or their equivalent) and also lysozyme and lyticase. In general, any combination of lytic enzymes that provide for decontamination in the methods of the invention is acceptable.

The enzymes can be provided in any amount that will provide the necessary lytic activity. For example, the final concentration of lysozyme in the enzyme cocktail (after addition of the sample to be decontaminated) can range from 100 µg/ml up to 25 mg/ml, and preferably 1-2 mg/ml lysozyme is present. Lyticase (e.g., zymolyase) is preferably present in amounts of at least 100 Units/mil or higher (for example, 1000 U/ml). Higher amounts of lyticase, while acceptable, might be prohibitively expensive. The other enzymes listed in Table 2 are useful when present at concentrations of about 0.1–2 mg/ml. In general, any concentration of lytic enzymes that provides for decontamination in the methods of the invention is acceptable.

In the methods of the invention the extraction conditions, including the buffer, temperature, ionic strength, and pH, preferably provide a condition in which the desired multiple enzymes function simultaneously. That is, the extraction condition is preferably such that all enzymes have at least some activity at the same time. In this embodiment, the condition of choice need not be optimal for all activities, but the condition should not be completely inhibitory to any one activity at all times. It is possible but less preferred to achieve the extraction in two or more steps, however, such that in the first step some of the desired enzymes are active, while in the subsequent step(s), conditions are changed such that previously inactive (or relatively inactive) enzymes are now active, or at least more active, for example, by changing temperature, ionic strength, buffer components, pH or metal composition as part of the extraction procedure. Appropriate conditions in which the lytic enzyme(s) is/are active are generally provided by the manufacturer and one of ordinary skill in the art can easily modify such conditions, as necessary, so that each desired lytic enzyme that is present in the composition is active.

When configuring a buffer system, some guidelines are preferably followed. First, when processing samples for the subsequent analysis of mycobacteria, N-acetyl-L-cysteine (NALC) (e.g., a reducing agent) is a preferred component of the system because it serves to liquefy biological samples, especially respiratory samples. Therefore, enzymes that are insensitive to reducing agents such as NALC are preferred if they are to be present in the same cocktail as the NALC. Second, it is advantageous to include citric acid in the cocktail because it serves to. chelate heavy metals that facilitate oxidation of NALC. The NALC/citrate containing buffer is preferred since this buffer acts synergistically with methods that use the betaine-like detergents of WO 95/27076. Therefore, enzymes without metal requirements are preferred. Third, the pH and ionic strength of the solution must also be such that the enzymes chosen have enzymatic activity. Additionally the presence of both lysozyme and lyticase activities are preferred, but the contamination rate may be further decreased by the addition of supplemental activities in some situations.

Configuring a buffer system for the desired use requires further considerations. For example, the two enzymatic activities of lyticase (endoglucanase and protease) have two different pH optima. The optimal pH for endoglucanase activity is approximately 6.0, while the protease activity is optimal around 8.5. The total lytic activity, however, appears to optimal around pH 8.0. Alternatively, lysozyme functions in a broad pH range, however, lytic activity is best in Tris buffer, as opposed to phosphate buffer (Metcalf et al., *J. Bacteriol.* 99:674–680 (1969)). Both lyticase and lysozyme are stable in the presence of reducing agents and chelators, as are mutanolysin and achromopeptidase. Lysostaphin, on the other hand, has a metal requirement and probably would not function in a citrate buffer. A Tris-citrate buffer (pH 7.6) is a preferred embodiment (if lysostaphin is not to be included as a component of the enzyme cocktail).

The buffered enzyme cocktail can be manufactured fresh daily, however, weighing out multiple milligram masses every day is tedious. Therefore, it is preferred that the cocktail (for example, buffer and enzymes) be made up as a concentrate and frozen in single use aliquots. Each aliquot is then thawed immediately prior to use, mixed with water and NALC, and then combined with the specimen for the decontamination step. If frozen aliquots are used, consideration must also be given to the sensitivity of each lytic enzyme to freezing. For example, lyticase loses 50% of its activity upon freezing (Scott et al., *J. Bacteriol.* 142:414–423 (1980)). The cocktail can also be provided in a powdered or lyophylized form that is dissolved immediately prior to use.

In the decontamination step(s), the specimen is incubated with a buffered solution (the cocktail) containing the appropriate enzymes or combination of enzymes, for a time and at a temperature that facilitates enzymatic activity. Preferably, the decontamination step is performed for a time and at a temperature that lowers or eliminates the viability of one or more contaminants, or that lowers or otherwise compromises the structureal integrity of one or more of the contaminants, for example, by degradation of the capsules of the contaminants. When it is desired to enhance the effect of the enzyme by the addition of an agent such as CB-18, the desired agent (such as CB-18) can be added to the preparation as in the standard procedure of WO 95/27076 (Example 1), with the enzyme composition, and incubated for 90 minutes at 37° C. with shaking. The specimen is then subjected to centrifugation at 4,000×g for 20 minutes at 30° C., decanted and the pellet resuspended in the solution of choice (e.g., water or buffer). The sediment is then subjected to the detection method(s) of choice (e.g., smear, culture, immunodiagnostic, and/or amplification). In this embodiment, the purpose behind the individual steps (e.g., liquefaction/decontamination, collection of the pellet and subjection of the sediment to the detection method of choice) changes very little. However, the composition, length and temperature of the steps can easily be modified to best process the specimen in a manner suitable for the ultimate detection method. This embodiment could be prohibitively expensive due to the large volume of betaine-like detergent employed in this embodiment and the amount of enzyme required to achieve the appropriate concentration.

In a preferred embodiment, the enzymatic decontamination step occurs prior to treatment with a betaine-like detergent such as CB-18. Example 5 exemplifies such an embodiment wherein the NALC liquefaction and enzyme decontamination steps are combined and precede treatment with CB-18. FIGS. 1–9 (Example 6) show in vitro examples wherein a single enzyme cocktail and buffer condition are shown to degrade yeast, fungi, molds, gram positive and some gram negative contaminants. FIGS. 10 and 11 show in vivo examples wherein authentic clinical specimens were treated using this same procedure.

In another preferred embodiment, the enzyme decontamination step follows any of the CB-18 procedures of WO 95/27076. For example, the specimen is first subjected to the standard CB-18 procedure, such as that described in Example 1, then, following centrifugation, the sediment is resuspended in water or buffer and the appropriate combination of lytic enzymes is added and incubated for a time and at a temperature that facilitates or brings about the decontamination. Such re-suspension fluid can also contain phospholipids, such as, for example, phophatidylcholine (e.g., lecithin), to neutralize the deleterious effect of combining some betaine-like detergents and antibiotics (as discussed in regard to Table 6, and as used in Example 9). The resulting specimen can then either be analyzed directly, or further processed, for example, with a detergent, preferably a betaine-like detergent, and most preferably CB-18, and then subjected to a secondary centrifugation to re-concentrate the specimen for analysis. Example 7 is an example wherein the enzymatic decontamination is preceded by treatment with CB-18, as in this embodiment. FIGS. 12–14 show in vitro examples wherein a single enzyme cocktail and buffer condition can degrade yeast, gram positive and gram negative contaminants.

Thus, in its broadest embodiment, the invention is directed to an enzymatic decontamination method for the processing of samples for the detection of a desired microorganism such as a mycobacteria, such method containing an enzymatic treatment step that compromises the viability of one or more undesired contaminating microbiological components, but that retains the viability of the desired microorganism, or that compromises the structural integrity in a manner that is itself harmful to the contaminating microorganism, or in a manner that enhances the harmful effects of other agents and so is secondarily harmful to the contaminating microorganism, so that levels of the contaminating microorganism are reduced or eliminated.

According to the invention, the viability of the undesired microorganisms is preferably reduced by enzymatically attacking the structural, metabolic or biological integrity of the undesired microorganisms, especially the structural integrity of the cell walls, to a degree sufficient to compromise the viability of the undesired microorganisms in a manner that impedes or otherwise destroys the ability of the microorganism to replicate or survive and in a manner that allows mycobacteria in the same sample to survive. In a further embodiment, a non-enzymatic component, for example a cofactor or ion, is added to facilitate or enhance the activity of the compromising activity of the enzymes in the method of the invention. In another embodiment, one or more enzymes can be added that facilitate or enhance the compromising activity of other components (enzymatic or non-enzymatic) in the extraction, such as detergents and/or antimicrobials, such that the presence of the enzyme and the second component acts in a manner that is beneficial to removing the undesired contaminants. In another embodiment, one or more enzymes may be added to the sample in an inactive form, and kept inactive, or relatively inactive, until a desired time in the processing, at which time the component or conditions necessary to the enzymatic activity may be provided. In a highly preferred embodiment, the undesired contaminants are rendered non-viable by lysing them.

In each of the embodiments, antibiotics or agents that act independently of the lytic enzymes can be added as desired, especially when such agents target a contaminant that is not otherwise compromised by the lytic enzyme treatment. Exposure to antibiotics can take place before, during or after treatment with one or more lytic enzymes.

In any of the embodiments of the invention, mechanical disruption techniques, such as sonication or other such techniques that enhance shear forces as understood in the art, and that act independently of the lytic anyzmes, can be employed as desired. Such techniques are especially useful when the technique is harmful to a contaminant that is not otherwise compromised by the lytic enzyme treatment. Exposure to such mechanical disruption can take place before, during or after treatment with one or more lytic enzymes, but after lytic enzyme treatement is most preferred.

Introduction of large amounts of heterologous (e.g., non-specific) nucleic acids, nucleases and/or proteases into the sediment, such as those associated with contaminants can reduce the efficiency of nucleic acid amplification by techniques such as PCR, thereby giving a false negative result. Similarly, introduction of large quantities of non-specific antigens and/or proteases associated with contaminants can reduce the sensitivity of immunological techniques, again causing a false negative result. In each of these scenarios, according to the invention, it is advantageous to specifically eliminate non-mycolic acid containing contaminants from the sediment. Thus, in an especially preferred embodiment, elimination of the undesired contaminants is achieved as a result of solubilizing some component of their cellular constituents, or lysing the organisms, thereby releasing their intracellular components into the processing media, in a manner such that the intracellular components are not preferably collected in the sediment (e.g., pellet fraction) following centrifugation. Any contaminant has the potential of interfering with culture techniques (e.g., cause a false positive result). At appropriate levels many contaminants can also interfere with either amplification or immunodiagnostics.

Due to the naturally slow growth of mycobacteria, non-mycobacterial contaminants are most problematic when it is desired to culture mycobacteria from the sediment and thus sediment is used as the source to inoculate culture media. The contaminants, since they often grow faster than the mycobacteria, can out-grow, or over-grow, the mycobacteria thereby confounding detection by culture. Alternatively, large numbers of contaminants can interfere with either nucleic acid amplification or immunodiagnostic techniques by overloading the detection system with large amounts of heterologous nucleic acids, nucleases, proteases and/or antigens.

One preferred embodiment of the invention herein involves first treating a specimen using the lytic enzyme methods of the invention, then treating with betaine-like reagents (e.g., CB-18) as described in WO 95/27076, and finally subjecting the resulting sediment to culture analysis using the 12B/PANTA system (CB-18/12B/PANTA), or modifications thereof, such as, for example, the 12B/PANTA/caz system used in Examples 2 and 9. The CB-18/12B/PANTA processing system for the processing of biological and inorganic samples for the detection of bacteria, and especially for the detection and/or identification of mycobacteria present in such samples, is also described in WO 95/27076.

Other readily available betaines useful in conjunction with the methods of the invention include the sulfobetaines and carboxybetaines, for example, the "SB"-series of detergents especially the highly purified (e.g., research grade) forms. Examples of carboxybetaines useful in the methods of the invention that utilize a methylene bridge ("carboxymethylbetaines": $R_4$=—$CH_2$—), a methylene linkage ($\alpha$=—$CH_2$—), and vary solely based on alkyl chain length include: $C_{10}$ (CAS® No. 2644-45-3), $C_{11}$ (CAS® No. 2956-38-9), $C_{12}$ (CAS® No. 683-10-3), $C_{13}$ (CAS® No. 23609-76-9), $C_{14}$ (CAS® No. 2601-33-4), $C_{15}$ (CAS® No. 23609-77-0), $C_{16}$ (CAS® No. 693-33-4), and $C_{18}$ (CAS® No. 820-66-6). There is a $C_{12}$-carboxymethylbetaine (CAS® No. 6232-16-2) example that is N,N diethyl ($R_3$=$R_4$=—$CH_2CH_3$); and an example in which the alkyl has a double bond: $C_{18:1}$ (CAS® No. 871-37-4). There are several carboxymethylbetaine examples in this subset in which a is an amidopropyl group. They include: $C_{12}$-amido (CAS® No. 4292-10-8), $C_{14}$-amido (CAS® No. 59272-84-3), $C_{16}$-amido (CAS® No. 32954-43-1), and $C_{18}$-amido (CAS® No. 617944-8). The $C_{18}$-amido (CAS® No. 6179-44-8) is of undefined structure because the alkyl is the "iso" form, which suggests that it branches in some undefined manner.

There are several amidopropyl carboxymethylbetaines in which the alkyl chain is derived from coconut oil, and differences are due to the method of preparation. Two examples in this category include CAS® Numbers 61789-39-7 and 61789-40-0. An example of cococarboxymethylbetaine is CAS® No. 68424-94-2. Other natural oil carboxymethyl derivatives include: ricinamidopropyl carboxymethylbetaine (CAS® No. 71850-81-2), and Tallow bishydroxyethyl glycinate (CAS® No. 7075046-8). There are also several carboxymethylbetaines that have been tested for which no CAS® No. has been given. These include: wheat germ oil-amidopropyl carboxymethylbetaine (Schercotaine WOAB: Scher Chemicals, Inc., Clifton, N.J.), babassuamidopropyl carboxymethylbetaine (Croda, Inc., Parsippany, N.J.), soyamidopropyl carboxymethylbetaine (Chembetaine S: Chemron Corp., Paso Robles, Calif.), and canloamidopropyl betaine (Hetaine CLA: Heterene, Inc., Patterson, N.J.). There are several examples in which the nitrogen in the amide linkage is the quaternary nitrogen (e.g., the linkage ($\alpha$) is a carbonyl). These include: $C_{11}$ (CAS® No. 66451-67-0), $C_{15}$ (CAS® No. 66516-99-2), and $C_{17}$ (CAS® No. 66451-68-1). Examples of carboxybetaines that utilize an ethyl bridge ("carboxyethylbetaine": $R_4$=—$CH_2CH_2$—), a methylene linkage ($\alpha$=—$CH_2$—), and vary solely based on alkyl chain length include: $C_{12}$ (CAS® No. 16527-85-8), $C_{13}$ (CAS® No. 132621-79-5), $C_{14}$ (CAS® No. 69725-38-3), $C_{16}$ (CAS® No. 42416-43-3), and $C_{18}$ (CAS® No. 30612-73-8). An example of a carboxyethylbetaine in which $R_2$ and $R_3$ are hydrogen atoms, under the appropriate conditions, is CAS® No. 1462-54-0 ($C_{12}$-beta alanine). Examples of carboxy betaines that utilize a propyl bridge ("carboxypropylbetaine": $R_4$=—$CH_2CH_2CH_2$—), a methylene linkage ($\alpha$=—$CH_2$—), and vary solely based on alkyl chain length include: $C_{11}$ (CAS® No. 150147-53-8), $C_{12}$ (CAS® No. 15163-30-1), $C_{14}$ (CAS® No. 146959-90-2), $C_{15}$ (CAS® No. 146959-91-3), $C_{16}$ (CAS® No. 71695-32-4), and $C_{18}$ (CAS® No. 78195-27-4). An example of a carboxybetaine that utilizes a butyl bridge ("carboxybutylbetaine": $R_4$=—$CH_2CH_2CH_2CH_2$—), and a methylene linkage ($\alpha$=—$CH_2$—), is: $C_{12}$ (CAS® No. 120139-51-7). Two examples of carboxy betaines that utilize a pentyl bridge ("carboxypentylbetaine": $R_4$=—$CH_2CH_2CH_2CH_2CH_2$—), and a methylene linkage ($\alpha$=—$CH_2$—), is: $C_{12}$ (CAS® No. 76392-97-7), and $C_{16}$ (CAS® No. 73565-98-7). An example of a carboxy betaine that utilizes a hexyl bridge ("carboxyhexylbetaine": $R_4$=—$CH_2CH_2CH_2CH_2CH_2CH_2$—), and a methylene linkage ($\alpha$=—$CH_2$—), is $C_{12}$ (CAS® No. 132621-80-8). There are several carboxybetaine examples in which a benzyl group is used as the bridge function ($R_4$=—$CH_2$—$C_6H_4$—). There are two $C_{12}$ examples, one in which the carboxy function is in the 4, or para, position (CAS® No. 71695-31-3), and one in which the carboxy function is in the 2, or ortho, position (CAS® No. 71695-34-6). There are two $C_{16}$ examples, one in which the carboxy function is in the 4, or para, position (CAS® No. 71695-33-5), and one in which the carboxy function is in the 2, or ortho, position (CAS® No. 71695-35-7). Therefore, "carboxybetaine-like" ("CB-like") shall include those betaine-like structures that utilize a carboxyl group as the anion ($\gamma$=—COO$\ominus$), as shown in Table 1, and shall include all possible combinations of $R_1$, $\alpha$, $R_2$, $R_3$, $\beta$, and $R_4$, as hereinbefore defined.

Most commercially available betaines are used to manufacture detergents, shampoos, cosmetics, and other toiletries. These betaines are derived primarily from natural oils such as coconut oil, tallow, wheat germ, babassu oil, castor oil, canola oil, soy bean oil, and rapeseed oil. The most common of these betaines includes cocoamidopropyl hydroxypropylsulfobetaine (CAS® No. 68139-30-0), cocoamidopropyl carboxymethylbetaine (CAS® No. 61789-37-9 and CAS® No. 61789-40-0), and cococarboxymethylbetaine (CAS® No. 68424-94-2). All these betaine-like detergents are useful in conjunction with the methods of the invention.

The composition and method of the invention are useful for the preparation of any sample suspected of containing a microorganism having mycolic acid structures in its outer membrane. Examples of such microorganisms include microorganisms having corynomycolic acid in their outer membrane (such as, for example, *Corynebacterium diphtheria*); microorganisms having nocardomycolic acid in their outer membrane (for example, *Nocardia asteroides*); and microorganisms having mycolic acid in their outer membrane (for example, *Mycobacterium tuberculosis*) (see also Funke, G. et al., *Clin. Micro. Rev.* 10: 125–159 (1997) for further discussions on coryneform bacteria (incorporated herein by reference)).

The composition and method of the invention are especially useful for the preparation of a sample to be assayed for the presence of any desired Mycobacterium group or complex or Mycobacterium species. Examples of such members of the Mycobacterium species include a mycobacterium complex such as *M. tuberculosis* (MTB) complex, *M. avium* (MAC) complex, MAIS complex and *M. fortuitum* complex, as well as fast growing and slow growing mycobacteria including specified and unspecified photochromogens, nonphotochromogens, scotochromogens, and especially *M. africanum, M. asiaficum, M. avium, M. bovis, M. bovis* (BCG), *M. butyricum, M. chelonae, M. duvalii, M. flavescens, M. fortuitum, M. gastri, M. gordonae, M. haemophilum, M. intracellulare, M. kansasii, M. leprae, M. lepraemurium, M. linda, M. lufu, M. marinum, M. malmoense, M. microti, M. mucoscum, M. nonchromogenicum, M. paratuberculosis, M. peregrinum, M. phlei, M. rhodochrous, M. scrofulaceum, M. shimoidei, M. simiae, M. smegmatis, M. szulgai, M. terrae, M. thermoresistible, M. triviale, M. tuberculosis, M. ulcerans, M. vaccae, M. xenopi*, and serovars thereof; *M. kansasii, M. marinum, M. simiae* and *M. asiaticum* and other photochromogens. *M. scrofulaceum, M. szulgai, M. xenopi, M. gordonae* and *M. flavescens* and other scotochromogens; *M. avium, M. intracellulare, M. gastri, M. malmoense, M. terrae* and *M. triviale* and other nonphotochromogens; *M. africanum, M. avium, M. bovis, M. haemophilum, M. intracellulare, M. kansasii, M. malmoense, M. marinum, M. microti, M. paratuberculosis, M. scrofulaceum, M. simiae, M. szulgai, M. tuberculosis,* and *M. xenopi* and other slow-growing (requiring more than seven days) mycobacterial species; *M. chelonei, M. flavescens, M. fortuitum, M. gordonae, M. leprae, M. neoaurum, M. phlei, M. smegmatis, M. terrae*, and *M. ulcerans* and other rapid-growing (requiring less than seven days) mycobacterial species. *M. tuberculosis, M. africanum, M. bovis, M. bovis* (BCG), and *M. microti* are the members of the *Mycobacterium tuberculosis* complex (MTB). *M. avium* and *M. intracellulare* are the members of the *Mycobacterium avium* complex (MAC); there are at least three distinct serologic groups of *M. avium*, and more than 25 serovars of *M. intracellulare*.

Examples of pathogens that can be extracted from samples prepared according to the invention and that are capable of causing diseases and conditions of heightened importance in testing include especially the causative agents of tuberculosis (*M. tuberculosis* complex) and leprosy (*M. leprae* (human leprosy) and *M. lepraemurium* (rodent leprosy)); *Mycobacterium avium* complex bacteria (important bird pathogens); *M. avium* (sometimes isolated from AIDS patients who are afflicted with a mycobacterial superinfection Nightingale, S. D. et al., *Jour. Infect. Dis.* 165:1082–1085 (1992)); *M. bovis* (of importance in veterinary medicine); *M. fortuitum* (a soil bacterium that has been isolated from lesions in animals and humans); *M. intracellulare* (opportunistic and especially seen in patients infected with the AIDS virus); *M. paratuberculosis* (of interest in the diagnosis of Crohn's disease (regional ileitis) in humans); *Mycobacterium kansasii* (a rare but devastating agent, generally associated with pulmonary disease); *Mycobacterium marinum* (infects cold-blooded animals and fish and has also been isolated from superficial granulomas on the extremities of humans); *Mycobacterium paratuberculosis* (the causative agent of Johne's disease in cattle; it is very slow growing and cultures must be held for 16 weeks before it can be assured that they are negative); and *M. ulcerans* (also of interest in human medicine). Many of the above and others have been discussed by Wayne, L. G. et al., *Clin. Micro. Rev.* 5:1–25 (1992), and Falkinham, O. *Clin. Micro. Rev.* 9:177–215 (1996) and are incorporated herein by reference.

Detecting the presence of organisms containing mycolic acid structures in their outer membranes in samples prepared by the method of the invention can be accomplished using techniques such as culture, nucleic acids amplification, and immunodiagnostics.

When it is desired to culture the mycobacteria from the sample, methods known in the art may be used. Examples of liquid media useful for mycobacterial culture include BACTEC 12B (also called "12B ") (Becton-Dickinson, Cockeysville, Md.), ESP® MYCO System II (DIFCO Laboratories, Detroit, Mich.) or MB/BacT® (Organon Teknika, Durham, N.C.). Examples of non-selective solid media useful for the culture of mycobacteria include Lowenstein-Jensen (L-J), 7H10 or 7H11. Examples of selective solid media useful for the culture of mycobacteria include L-J Gruft, Mycobactosel or 7H11 1-selective. Whereas the selective solid media is generally preferred, relative to the non-selective media, the liquid culture media, which is generally more sensitive, is preferred with the methods of the invention. Commercial preparations of antibiotic supplements for use in conjunction with the aforementioned liquid culture systems include PANTA (Becton-Dickinson, Cockeysville, Md.), PVNA (DIFCO Laboratories, Detroit, Mich.), and MAS (Organon Teknika, Durham, N.C.), respectively. Each of these culture systems can be modified to incorporate different or additional antibiotics to optimize diagnostic performance in conjunction with the methods of the invention. For example, in Example 1 modification of the PANTA formulation to include ceftazidime is described. Most laboratories use the 12B/PANTA system. The methods of the invention can easily be used in conjunction with any of these culture systems.

Immunodiagnostic techniques rely on the interaction of mycobacterial antigen(s) and one or more antibodies provided in the assay reagents. Immunodiagnostic techniques may be specific for a certain member of the mycobacteria, or may be capable of detecting two or more members.

Detection techniques such as nucleic acid amplification (for example, using polymerase chain reaction (PCR) technology) and immunodiagnostics rely on the interaction of specific mycobacterial component(s) with one or more agents provided in the respective assay. For example, nucleic acid amplification techniques rely on the interaction of specific mycobacterial nucleic acid sequences and the complementary primer(s) provided in the assay reagents.

Some examples of nucleic acids amplification techniques useful in conjunction with the methods of the invention include, but are not limited to, polymerase chain reaction (PCR), transcription mediated amplification (TMA), strand displacement amplification (SDA), and ligase chain reaction (LCR) techniques. Kits for the first two examples (e.g., PCR and TMA) are commercially available from Roche Molecular Systems (13ranchburg, N.J.) and Gen-Probe, Inc. (San Diego, Calif.), respectively. The methods of the invention can be used in conjunction with any of desired detection technique.

Having now fully described the invention, it will be understood by those with skill in the art that the invention may be performed within a wide and equivalent range of conditions, parameters and the like, without affecting the spirit or scope of the invention or any embodiment thereof. All references cited herein are fully incorporated herein by reference.

EXAMPLES

Example 1

CB-18 Processing: Incidence of Gram Negative Contamination

Discarded respiratory specimens (n=277) from Quest Diagnostics, Inc. (QDI), Baltimore were collected and processed with CB-18 according to the procedure below. This procedure is based on the methods of Thornton as described in WO 95/27076 and is designed as a primary processing methodology for the isolation of mycobacteria from all respiratory specimens (e.g., sputa, bronchial washes, ravages and induced sputa). Manufacture of the reagents for this procedure are described at the end of this example.

(1) Place 1–10 mls of sputum or bronch-wash in a 50 ml conical tube. NOTE: While respiratory specimens are the predominant specimen type expected to be used in conjunction with the procedure described here, other specimen types such water, soil, tissue, fecal and other specimens can be adapted for use in conjunction with the procedure below. Some of these specimens might first be clarified by resuspending in water or buffer and passing the mixture over a Spin-X II column fitted with a 20–60 micron frit (Corning Costar, Boston, Mass.). Such a column might also contain a matrix, such as Sephadex® (G-50: Pharmacia, Piscataway, N.J.) or an equivalent resin, to enhance purification. Any specimen could then be treated as described below.

(2) To the specimen add an equal volume of 0.5% NALC liquefaction solution (see below: 0.5% NALC/25 mM sodium citrate) and vortex well.

(3) Incubate at room temperature for 10 minutes (vortex at about 5 minutes, and then just before the next step).

(4) Open the tube and add sterile, filtered water to the specimen to a final volume of approximately 35 mls.

(5) Add 4 mls of a betaine-like detergent (10× CB-18 Buffer for example (see below): 10×CB-18=10 mM CB-18, 0.5 M Tris-HCl pH 8.0, 50 mM NALC, and 1 mM NaCl).

(6) Vortex well to completely mix the specimen.

(7) Incubate at 37° C. for 90 minutes with shaking (140 rpm). (8) Vortex and then centrifuge specimens at 4,000×g for 20 minutes at 30° C.

(9) Decant the tubes completely and add 500 µl of sterile water or buffer to the specimen.

(10) Resuspend the pellet completely and prepare the sediment for detection, such as by culture or amplification.

The sediments were planted on BACTEC 12B liquid media supplemented with PANTA (12B/PANTA) (Becton Dickinson, Cockeysville, Md.). All contaminants were identified by morphology and/or gram stain and then differentiated as either oxidase/catalase, positive or negative. Contaminants were then speciated, and antibiotic sensitivities determined, using MicroScan panels (Dade International, Sacramento, Calif.). The results are shown in Table 3.

TABLE 3

Identification of BACTEC 12B/PANTA Contaminants
(n = 277)

| Group | # | % |
| --- | --- | --- |
| Gram Negative | 48 | 84.2% |
| Gram Positive | 5 | 8.8% |
| Yeast | 3 | 5.3% |
| Fungi | 1 | 1.8% |
| Total: | 57 | |

From 40 Patients: Contamination = 14.4%

Table 3 shows that of the 277 specimens processed, 57 contaminants were isolated from 40 specimens. The overall contamination rate on a per specimen basis was 14.4% (40÷277). Of the 57 contaminants identified, 84.2% were gram negative, 8.8% were gram positive, 5.3% were yeast, and 1.8% were fungi. Closer examination of the gram negatives revealed that 31 (64%) of the 48 were gram negative rods. The most common isolates were *Providencia stuartii* (n=13), *Pseudomonas* species (n=11), and *Proteus mirabilis* (n=7). Examination of the sensitivity data showed that 40 of the 48 gram negative bacteria were sensitive to ceftazidime at 8 µg/ml.

Table 3 suggests that the predominant problem encountered with respiratory specimens processed according to WO 95/27076 (e.g., CB-18) is the occurrence of gram negative organisms (e.g., >84%). In other words, significantly impacting the contamination rate would require a reduction in the incidence of gram negative organisms. As a result of these data and other experiments it was decided that the antibiotic supplement PANTA should be fortified with ceftazidime (8 µg/ml final) in an attempt to control this gram negative contamination. Based on parallel experiments it was thought that ceftazidime would reduce the incidence of gram negative contamination without significantly impacting the viability of the mycobacteria (data not shown). Examples 2, 3, and 4 describe selected results of processing respiratory specimens with CB-18 and culturing in 12B/PANTA/caz.

Preparation of 10×CB-18 Buffer (1) 20× Buffer Salts: 1M Tris-HCl pH8.0, 2 mM NaCl

| Tris Base (121.14 gr/mole) | 54.27 gr |
| --- | --- |
| Tris HCl (157.64 gr/mole) | 87.02 gr |
| NaCl | 0.117 gr |
| Add Water to: | 1 liter |

(i) Place approximately 250 mls of water in a 1 liter graduated cylinder.
(ii) Add the Tris base (Sigma, St. Louis, Mo., Cat. #: T 1503), Tris-HCl (Sigma, St. Louis, Mo., Cat. #: T3253) and NaCl (Sigma, St. Louis, Mo., Cat. #: S 7653) and mix (NOTE: use sterile, filtered water (e.g., GIBCO/BRL, Gaithersburg, Md., Cat. #: 15230-022)).
(iii) Add the remaining water to 1 liter and ensure complete mixing. (iv) Check the pH by removing a small aliquot. The pH should be ±0.2 pH units.
(v) Filter sterilize (0.22 µ filter), divide into 50 ml aliquots, and store at room temperature.

(2) 100× CB-18 Stock Solution: 100 mM CB-18

| *CB-18 (383 gr/mole) | 1.915 gr |
| --- | --- |
| Isopropanol:Water (1:1) to: | 50 mls |

*CB-18: N,N-dimethyl-N-(n-octadecyl)-N-(3-carboxypropyl)ammonium inner salt (CAS ® No. 78195-27-4)

(i) Mix 25 mls of analytical grade isopropanol (Baxter, McGaw Park, Ill., Cat. #: 3043-1 NY) with 25 mls of water in a graduated cylinder to prepare 50 mls of 1:1, isopropanol:water (NOTE: use sterile, filtered water (e.g., GIBCO/BRL, Gaithersburg, Md., Cat. #: 15230-022)).
(ii) Transfer 25 mls of the Isopropanol:Water (1:1) solution to a 50 ml conical tube.
(iii) Weight-out 1.915 grams of CB-18 and place it in the graduated cylinder with 25 mls of the remaining isopropanol:water (1:1). Mix by swirling.
(iv) Add more of the Isopropanol:Water (1:1) solution, up to about 40, mls and swirl gently. Let the solution sit for about 20 minutes and swirl gently about every 5 minutes.
(v) When the CB-18 has dissolved (about thirty minutes total) bring the final volume up to 50 mls with the Isopropanol:Water (1:1) solution and mix by inversion.
(vi) Divide the solution into two sterile plastic 50 ml conical tubes and store at room temperature.

(3) 10× CB-18 Buffer (i) Determine the number of specimens to be processed, insert this number in the chart below (add one (1) to this number to ensure enough buffer), calculate the final amounts of each component required and prepare the appropriate amount of 10× CB-18 as described below.

| Component | Multiplication Factor | | | Final Amount |
| --- | --- | --- | --- | --- |
| 20X Buffer Salts | 2 mls | × | Number | = |
| 100X CB-18 | 400 µl | × | of | = |
| NALC (163.2 gr/mole) | 0.033 gr | × | Specimens | = |
| Add Water to | 4 mls | × | plus one | = |

(ii) Immediately prior to use combine the 20× Buffer Salts, NALC (Fluka, Ronkonkoma, N.Y., Cat. # 01039), and 100× CB-18 and bring up to volume with sterile, filtered water (NOTE: use sterile, filtered water (e.g., GIBCO/BRL, Gaithersburg, Md., Cat. #: 15230-022)). NOTE: At any point in this procedure if precipitate is present in the buffer, DO NOT USE. The solution should be kept warm during storage and use (e.g., greater than 20° C). Do not refrigerate this solution.

Preparation of 0. 5% NALC Liquefaction Solution
(1) 10× Na-Citrate Stock: 0.25 M sodium citrate dihydrate

| Trisodium Citrate dihydrate 294.1 gr/mole | 7.35 gr |
| --- | --- |
| Add Water to: | 100 mls |

(i) Place approximately 25 mls of water in a 100 graduated cylinder (NOTE: use sterile, filtered water (e.g., CIBCO/BRL, Gaithersburg, Md., Cat. #: 15230-022)).
(ii) Add the trisodium citrate dihydrate (Sigma, St. Louis, Mo., Cat. #: C 3434) and mix by swirling. Add the remaining water to 100 mls and mix by inversion.

(iii) Sterilize by filtration (0.22 µ filter) and aliquot into 50 ml conicals. Store at room temperature.

(2) 0.5% NALC Liquefaction Solution (made fresh daily):

(i) Determine the approximate volume of NALC liquefaction solution required.

(ii) Combine the 10× Na-Citrate stock and NALC (Fluka, Ronkonkoma, N.Y., Cat. #: 01039) in a 50 ml conical tube or graduated cylinder, and bring to the final volume with water (NOTE: use sterile, filtered water (e.g., GIBCO/BRL, Gaithersburg, Md., Cat. #: 15230-022)).

(iii) Use immediately and discard the unused portion.

| Approx. # Specimens | 3–10 | 7–25 | 12–37 | 15–50 |
|---|---|---|---|---|
| 10X Na-Citrate Stock | 2.5 mls | 5 mls | 7.5 mls | 10 mls |
| NALC (163.2 gr/mole) | 0.12 gr | 0.25 gr. | 0.38 gr. | 0.5 gr. |
| Add Water to: | 25 mls | 50 mls | 75 mls | 100 mls |

Preparation of Ceftzidime Stock and 12B/PANTA/caz (1) Ceftazidime Stock (36 mg/ml)

| Ceftazidime | 72 mg |
|---|---|
| 1 M Na-Bicarbonate | 85.6 µl |
| Add Water to: | 2 mls |

(i) In a 2 ml volumetric flask mix 1 ml of the water and the 1 M sodium bicarbonate (Sigma, St. Louis, Mo.: Cat. #: S 6297 (mix 8.40 grams in 100 mls water, sterile filter, and store frozen in 10 ml and 1 ml aliquots)) (NOTE: use sterile, filtered water (e.g., GIBCO/BRL, Gaithersburg, Md., Cat. #: 15230-022)).

(ii) Add the ceftazidime (Sigma, St. Louis, Mo.: Cat. #: C 3809) and immediately bring the volume up to 2 mls with water.

(iii) Gently mix by inversion until the solution is clear. DO NOT heat the solution above room temperature (e.g., do not warm the solution in your hands.)

(iv) Immediately aliquot 50 µl portions into 1.5 ml microfuge tubes and store at −70° C. until use.

(2) Fortification and Use of PANTA/caz (i) Remove the lyophilized PANTA and reconstitution fluid (RF) from the refrigerator, and one 50 µl aliquot of ceftazidime stock (36 mg/ml) from the freezer.

(ii) When the ceftazidime has melted, use a 5 ml syringe and add 1 ml of RF to the ceftazidime stock. Mix by drawing into the syringe and expelling one time. Using the syringe, transfer the entire contents to the PANTA bottle.

(iii) Add 4 more milliliters of RF to the PANTA bottle (final volume=5 mls). Label "PANTA/caz."

(iv) Add 100 µls of PANTA/caz to each 12B bottle prior to use (add the antibiotic within 2 hours of specimen addition.)

(v) Store the unused portion at −20° C. Discard after 48 hours (e.g., do not freeze-thaw more than 1 time.)

Example 2

CB-18 Pilot Study

CB-18 was used to process respiratory specimens for the detection of mycobacteria (acid fast bacilli: AFB). Respiratory specimens (n=573) were split and collected from the TB-laboratories of QDI-Baltimore, as well as QDI-Teterboro, D.C. Bureau of Laboratories, Johns Hopkins Hospitals, and the University of Maryland at Baltimore. The host site split specimens such that half of each specimen was processed at the site by the standard NALC/NaOH method (Kent, P. T. et al., "Public Health Mycobacteriology," in *A Guide for the Level III Laboratory*, U. S. Department of Health and Human Service, Centers for Disease Control, (1985) pp. 31–46) and the other half of each specimen was sent to the QDI-Baltimore facility. Following transport to QDI-Baltimore specimens were processed with CB-18 on a daily basis as described in Example 1. The sediments were planted on 12B/PANTA liquid media, supplemented with ceftazidime (8 µg/ml: herein known as "12B/PANTA/caz"), and 7H11-selective slants. All 12B/PANTA/caz contaminants were identified by morphology and/or gram stain and then differentiated as either oxidase/catalase, positive or negative. Contaminants were then speciated, and antibiotic sensitivities determined, using MicroScan panels (Dade International, Sacramento, Calif.). The results are shown in Table 4.

TABLE 4

CB-18 Pilot Study Contaminants
(n = 573)

| Group | # | % |
|---|---|---|
| Gram Negative | 55 | 38.2% |
| Gram Positive | 29 | 20.1% |
| Yeast | 50 | 34.7% |
| Fungi | 9 | 6.2% |
| Unknown | 1 | 0.7% |
| Total: | 144 | |

From 119 Patient: Contamination = 20.8%

Table 4 shows that the contamination rate for CB-18 processed specimens on a per specimen basis was 20.8% (119÷573). The comparative liquid culture contamination rate (e.g., 12B/PANTA) for NaOH processed specimens was approximately 7.5% (data not shown). Analysis of Table 4 revealed that 38.2% of the isolates were gram negative, 20.1% were gram positive, 34.7% were yeast, and 6.2% were fungi. One specimen was lost prior to identification. Further examination of the gram negatives revealed the most common isolates as Pseudomonas species (n=31), *Xanthomonas maltophilia* (n=5), and *Serratia marcescens* (n=5). Among the gram positive isolates, there were 16 Staphylococcus species, and 10 gram positive rods (probably Bacillus species).

Table 4 shows a remarkable dichotomy relative to the data of Table 3. For example, while the overall contamination rate was not impacted by inclusion of ceftazidime (e.g., the contamination increased from 14.4% to 20.8%), the gram negative incidence fell rather markedly (e.g., from 84.2% to 38.2%). The data of Table 4 suggested that either there was a significant difference in the nature of the specimens sent to the AFB lab for analysis versus those sent for general microbiological analysis, or the dynamics of contamination was affected by incorporation of ceftazidime. If the former hypothesis is correct, then the suggestion is that a more significant impact on the contamination rate can be achieved by focusing on eliminating the gram positive and mycologic (e.g., yeast and fungi) contaminants.

Example 3

Contaminants from the Baltimore Laboratory

The subset of specimens in the CB-18 Pilot Study (see Example 2 and Table 4) that were derived from the Baltimore laboratory (n=171) were segregated and the results shown in Table 5.

TABLE 5

CB-18 Study Contaminants - Baltimore
(n = 171)

| Group | # | % |
|---|---|---|
| Gram Negative | 9 | 25.7% |
| Gram Positive | 6 | 17.1% |
| Yeast | 17 | 48.6% |
| Fungi | 3 | 8.6% |
| Total: | 35 | |

From 31 Patients: Contamination = 18.1%

Table 5 shows that the contamination rate for CB-18 processed specimens from the Baltimore AFB lab was 18.1%. The comparative liquid culture contamination rate (e.g., 12B/PANTA) for NaOH processed specimens from the Baltimore AFB lab was approximately 6.4%. Table 5 again shows the dichotomy relative to the data of Table 3: The overall contamination rate did not appear to be impacted by the inclusion of ceftazidime (e.g., contamination increased from 14.4% to 18.1%), and the gram negative incidence was much reduced (e.g., from 84.2% to 25.7%).

The data of Table 5 support the hypothesis that there was a difference in the nature of the specimens sent to the AFB lab for analysis versus those sent for general microbiological analysis. While it could be argued that the source of specimens used to generate the data in Tables 3 and 4 are not directly comparable (e.g., they were derived from different laboratories), the specimens used to generate the data of Tables 3 and 5 were both from the Baltimore laboratory, and as such are directly comparable. For example, they are from the same laboratory, with the difference being that the one group of specimens was culled exclusively from the main microbiology laboratory (Table 3), and the other group being culled exclusively from the TB-lab (Table 5). In conclusion, Table 5 supports the notion that when using the methods of WO 95/27076 a more significant impact on the contamination rate can be achieved by focusing on the gram positive and mycologic contaminants.

Example 4

Interaction of CB-18 and PANTA/caz

The sensitivity of liquid and solid culture of the two different processing methods used in the CB-18 Pilot Study (supra) was examined. The data of Table 6 break down the number of AFB culture positive specimens isolated by the given culture method (e.g., liquid vs. solid), for a given processing method (e.g., NaOH vs. CB-18), as well as by smear result of that processing method. There were 106 AFB positive specimens in the study. There were 8 M. gordonae isolates. All were discrepant, smear negative and split equally between the two methods (e.g., the 4 that were isolated by NaOH were missed by CB-18, and vice versa). Since M. gordonae isolates are considered contaminants of limited clinical significance (Wayne, L. G., et al., Clin. Microbiol. Rev. 5:1–25 (1992)), they were omitted from the following analyses: therefore 98 AFB culture positive specimens were analyzed. NaOH processing identified 61 specimens: 45 were positive by both liquid and solid culture, 15 were positive by liquid only, and 1 was positive on solid media only. CB-18 processing identified 89 specimens: 42 were positive by both liquid and solid culture, 15 were positive by liquid only, and 32 were positive on solid media only. The sensitivity of liquid culture when processed by NaOH and CB-18 was 98.4% and 64.0%, respectively. The sensitivity of solid media when processed by NaOH and CB-18 was 75.4% and 83.1%, respectively. The overall culture sensitivity of the NaOH processing method was 62.2%, and the overall culture sensitivity when processed by CB-18 was 90.8%. While CB-18 processing increased culture sensitivity by approximately 46%, there was a reversal in the respective sensitivities of the different culture methods (e.g., liquid vs. solid culture).

TABLE 6

Comparison of Liquid and Solid Culture Sensitivities

| | | Culture Result | | | | Sensitivity | |
|---|---|---|---|---|---|---|---|
| | | Liquid & Solid | Liquid Only | Solid Only | AFB Sum | Liquid | Solid |
| NaOH | Smear ⊕ | 31 | 6 | 0 | 37 | 100% | 83.8% |
| | Smear ⊖ | 14 | 9 | 1 | 24 | 95.8% | 62.5% |
| | Total | 45 | 15 | 1 | 61 | 98.4% | 75.4% |
| CB-18 | Smear ⊕ | 38 | 4 | 14 | 56 | 75.0% | 92.9% |
| | Smear ⊖ | 4 | 11 | 18 | 33 | 45.4% | 66.7% |
| | Total | 42 | 15 | 32 | 89 | 64.0% | 83.1% |

The expected result is that seen for NaOH processed specimens: liquid culture was approximately 31% more sensitive than culture on solid media. In contrast, when specimens were processed using CB-18 (as described in Example 1), and planted on 12B/PANTA/caz and 7H11-selective slants, the solid media was approximately 30% more sensitive (Table 6).

The reversal in liquid-solid culture sensitivity among CB-18 processed specimens (Table 6) suggested that the combination of CB-18 with the antibiotics in the PANTA/ceftazidime supplement might be deleteriously impacting the sensitivity of liquid culture. For example, comparing the solid culture sensitivity of smear positive and smear negative specimens of the two different processing methods showed a marked similarity. Sensitivity among smear positive specimens was 34% higher than smear negative specimens when processed by NaOH, and 39% higher when processed by CB-18. The same examination of the liquid culture data showed a minor difference in sensitivity between smear positive and smear negative specimens when processed by NaOH (e.g., a 4% difference), but a striking difference among the same group processed by CB-18 (e.g., a 65% difference). The 75% liquid culture sensitivity among smear positive specimens processed by CB-18 was unexpected and unusual, and is in marked contrast to 100% sensitivity of NaOH-liquid culture. Stone, B. L. et al., Jour. Clin. Micro. 35:1030-1031 (1997) also showed that the liquid culture sensitivity of smear positive specimens (when processed by NaOH) was 99.3%. This study had a very large number of smear positive specimens (n=439).

The 14 smear positive specimens missed by CB-18/12B/PANTA/caz can be attributed to the effects of combining CB-18 with antibiotics in the PANTA/ceftazidime supplement. This effect seems to be most pronounced in a few mycobacterial isolates and absent in most isolates. While this effect may be overcome with lecithin, the conclusion is that CB-18 may be sensitizing some mycobacteria to antimicrobials that they would not be susceptible to under normal circumstances. As such further attempts to modify the antimicrobial supplement become very unattractive due to the amount of work required to characterize antibiotic formulations and screen isolates. In other words, alternative methods to confront the contamination problem were more desirable.

Example 5

Digestion with Lytic Enzymes Prior to Processing with Betaine-Like Detergents The first preferred embodiment for the enzyme/CB-18 decontamination of clinical specimens is as follows. Suggested formulations can be found at the end of this example.

(1) Place 1–10 mls of sputum or bronch-wash in a 50 ml conical tube.

NOTE: While respiratory specimens are the predominant specimen type expected to be used in conjunction with the procedure described here, other specimen types such water, soil, tissue, fecal and other specimens can be adapted for use in conjunction with the procedure below. If desired some of these specimens can first be clarified by resuspending in water or buffer and passing the mixture over a Spin-X II column fitted with a 20–60 micron frit (Corning Costar, Boston, Mass.). Such a column can also contain a matrix, such as Sephadex® (G-50: Pharmacia, Piscataway, N.J.) or an equivalent resin, to enhance purification. Any specimen can then be treated as described below.

(2) To the specimen add an equal volume of lytic enzyme solution (the 2× LZCT formulation for example: 1× LZCT= 50 mM Tris-HCl, 12.5 mM citrate pH 7.6, 30 mM NALC, 3 mM NaCl, 1 mg/ml lysozyme, 500 units/ml zymolyase, 0.1 mg/ml Cytophaga extract, and 1 mg/ml Trichoderma extract) and vortex well.

(3) Incubate for approximately 20 minutes at 37° C. with gentle shaking. (This step may require up to 60 minutes to achieve maximal lysis. Incubation might also be accomplished at room temperature.)

(4) Open the tube and add sterile, filtered water to the specimen to a final volume of approximately 35 mls.

(5) Add 4 mls of 10× buffered betaine-like detergent solution (e.g., the 10× CB-18 formulation described in Example 1: 10× CB-18=10 mM CB-18, 0.5 M Tris-HCl pH 8.0, 50 mM NALC, 1 mM NaCl, or equivalent).

(6) Vortex well to completely mix the specimen.

(7) Incubate at 37° C. for 90 minutes with shaking (140 rpm).

(8) Vortex well and then centrifuge specimens at 4,000×g for 20 minutes at 30° C.

(9) Decant the tubes completely and add 500 μl of sterile water or buffer to the specimen.

(10) Resuspend the pellet completely and prepare the sediment for detection such as by culture, nucleic acids amplification, or immunodiagnostic techniques.

(1) 20× Buffer Stock

One example of a buffer formulation that can be used in the methods of the invention is described below. This formulation would provide a 20× concentrate containing 1 M Tris-HCl, 250 mM citrate pH 7.6, and 30 mM NaCl. Additional components can be included as necessary, or exchanged as required, and optimized for use in conjunction with the desired enzymes.

| | |
|---|---|
| Tris Base (121.14 gr/mole) | 10.98 gr |
| Tris HCl (157.64 gr/mole) | 1.48 gr |
| Citric Acid-monohydrate (210.1 gr/mole) | 5.25 gr |
| NaCl (58 gr/mole) | 170 mg |
| Add Water to: | 100 mls |

(a) Place approximately 75 mls of sterile, filtered water in a graduated cylinder with a stir bar (NOTE: use sterile, filtered water (e.g., GIBCO/BRL, Gaithersburg, Md., Cat. #: 15230-022))

(b) Add the Tris base (Sigma, St. Louis, Mo. Cat. #: T 1503), Tris-HCl (Sigma, St. Louis, Mo., Cat. #: T 3253), citric acid (Sigma, St. Louis, Mo., Cat. #: C 1909) and NaCl (Sigma, St. Louis, Mo., Cat. #: S 7653) and mix.

(c) Add the remaining water to 1 liter, dissolve the components and ensure complete mixing.

(d) Check the pH by removing a small aliquot (10 mls). The pH should be ±0.2 pH units.

(e) Filter sterilize (0.22 μ filter), and immediately manufacture the enzyme stock (below).

(2) 10× Enzyme Stock:

One example of a lytic enzyme cocktail that can be used in the methods of the invention is described below. The formulation described would provide a 10× concentrate containing 10 mg/ml lysozyme, 5000 units/ml zymolyase (a.k.a. lyticase), 1 mg/ml Cytophaga extract, and 10 mg/ml Trichoderma extract. This formulation, herein referred to as "LZCT", can be modified to change the existing formulation, or include additional lytic enzymes as necessary.

| | |
|---|---|
| 20X Buffer Stock | 50 mls |
| Lysozyme | 1 gram |
| Zymolyase (a.k.a., Lyticase) | 500,000 units |
| Enzyme A (e.g., *Trichoderma harzianum* Extract) | 1 gram |
| Enzyme B (e.g., Cytophaga Species Extract) | 100 mgrams |
| Enzyme C (optional) | |
| Add water to: | 100 mls |

(a) Place approximately 50 mls of filtered 20× Buffer Stock in a graduated cylinder.

(b) Add lysozyme (Sigma, St. Louis, Mo., Cat. #: L 6876), lyticase (Sigma, St. Louis, Mo., Cat. #: L 4025), Trichodenna extract (Sigma, St. Louis, Mo., Cat. #: L 2265), Cytophaga extract (Sigma, St. Louis, Mo., Cat. #: L 9893 or L 1784), and/or other enzyme components as desired, and slowly mix.

(c) Add sterile filtered water to 100 mls and ensure complete mixing (about 5 minutes). The solution will be a clear, but brown (Note: use sterile, filtered water (e.g. GIBCO/BRL, Gaithersburg, Md., Cat. #: 15230-022)). NOTE: When using some lytic enzyme extracts, such as the Rhizoctonia extract (Sigma, St. Louis, Mo., Cat. #: L 8757), large amounts of insoluble material may be present.

(d) Immediately distribute the enzyme solution into 1 to 2 ml aliquots and place at −20° C. Do not let this solution sit at room temperature.

(3) 2× Enzyme Decontamination Solution (made fresh daily)

Determine the volume of Enzyme decontamination solution (e.g., 2× LZCT) required and follow the instructions below.

| Approx. # of Specimens | 1–5 | 3–10 | 7–25 | 12–37 |
|---|---|---|---|---|
| 10X Enzyme Stock | 2 ml | 6 mls | 12 mls | 18 mls |
| NALC (163.2 gr/mole) | 0.05 gr | 0.15 gr. | 0.30 gr. | 0.45 gr. |
| Add Water to: | 10 mls | 30 mls | 60 mls | 90 mls |

(a) Place approximately half of the water into a 50 ml conical tube or a graduated cylinder (NOTE: use sterile, filtered water (e.g., GIBCO/BRL, Gaithersburg, Md., Cat.#: 15230-022)).

(b) Add the appropriate amount of 10× Enzyme Stock (e.g., 10× LZCT) and mix.

(c) Add the appropriate amount of NALC (Fluka, Ronkonkoma, N.Y., Cat. #: 01039) and dissolve.

(e) Use immediately and discard the unused balance.

This solution should be used immediately. It should not be permitted to sit for more than 15 to 20 minutes at room temperature before use. In addition, with each new lot manufactured sterility tests should be run in which the enzyme cocktail is checked for inherent contaminants. For example, when testing achromopeptidase (Sigma, St Louis, Mo., Cat. #: A 3547) exceptionally high levels of contamination were observed that were caused by the presence of viable organisms present in the extract itself In those instances where contamination was observed, filtration may be necessary. If filtration is required it is recommended that a syringe type filter (0.22 $\mu$) be used on a daily basis. Filtering the large stock caused foaming which could be detrimental to the enzymes.

Example 6

Pre-digestion of Specimens with LZCT Enzyme Decontamination Solution

The first preferred embodiment was outlined in Example 5. The procedure described in Example 5 was used below to pre-digest prototype contaminants and clinical specimens with LZCT. The enzyme reagents used are described in Example 5, and the CB-18 components used are described in Example 1.

Initial attempts to examine the spectrum of activity of LZCT utilized purified strains of organisms designed to exemplify potential contaminants. Each prospective contaminant was purified, identified by standard techniques, and grown on the appropriate culture media. Replicate tubes of each contaminant were prepared by combining a mass (e.g., from solid media) or 500 $\mu$l (e.g., from liquid cultures) of the purified contaminant with sterile filtered water to a final volume of 2 mls. The suspension was then passed over a 20 micron filter to eliminate clumps. To the individual slurries were added 8 mls of autoclaved bronchial-washes (10 mls final volume). These mock specimens were then split into 2 ml aliquots for processing. Sterile bronchial-washes were used in an effort to simulate a clinical specimen. For example, sterile bronch-wash would have the consistency and composition of an actual clinical specimen but would not provide whole, and/or live organisms that might interfere with in vitro culture or microscopic analysis.

For each isolate four replicates were started as follows. The first replicate was unprocessed ("Not Processed"), the second replicate was treated with a modified version of the standard NALC/CB-18 procedure of WO 95/27076 as described in Example 1 ("NALC/CB-18"). The third replicate was treated with LZCT, but no CB-18 ("LZCT"), and the fourth replicate was first treated with LZCT and then CB-18 according to a modified procedure of that described in Example 5 ("LZCT/CB-18").

The unprocessed tube was brought to 10 mls with sterile filtered water, mixed, and 30 $\mu$l aliquots taken for microscopic analysis and photography as described below. The procedures used to process the remaining tubes (e.g., the NALC/CB-18, LZCT, and LZCT/CB-18 tubes) were modified as follows. An equal volume (e.g., 2 mls) of either 0.5% NALC liquefaction solution (0.5% NALC, 1.45% citrate) or 2×LZCT (1× LZCT=50 mM Tris-HCl, 12.5 mM citrate pH 7.6, 3 mM NaCi, 30 mM NALC, 1 mg/ml lysozyme, 500 units/ml zymolyase, 0.1 mg/ml Cytophaga extract, and 1 mg/ml Trichoderma extract) was added to the appropriate mock specimen and incubated at 37° C. for 20 minutes with shaking (140 rpm). The NALC/CB-18 and LZCT/CB-18 tubes were brought to 9 mls with sterile filtered water and then brought to a final volume of 10 ms with 1 mil of 10× CB-18 (10× CB-18=10 mM CB-18, 500 mM Tris-HCl pH 8.0, 50 mM NALC, 1 mM NaCl). The LZCT tube was brought to 10 mls with 1× Tris-citrate buffer (50 mM Tris-HCl, 12.5 mM citrate pH 7.6, 3 mM NaCl). All tubes were then incubated at 37° C. for 90 minutes with shaking (140 rpm). Following this incubation 30 $\mu$l aliquots were taken for microscopic analysis and photography as described below.

Microscopic analysis and photography were performed as follows. All yeasts, molds, gram negative and gram positive organisms were gram stained using the BBL Gram Stain kit (BBL, Cockeysville, Md.) according to the instructions of the manufacturer (see also Chapin, K. In: *Manual of Clinical Microbiology* $6^{th}$ Edition, Murray, P. R. et al., eds. ASM Press, Washington, D.C. (1995) pp 39–41 for the gram stain procedure). All slides were examined using a Nikon Labophot-2 microscope with a Nikon FX-35DX camera attachment. Slides were examined with a 10× eyepiece and 100× oil immersion objective lens. The camera was attached using an 2. 5X F-tube trinocular attachment. All exposures were shot at approximately 250× magnification. Photographs were taken using Kodak Ektachrome 160T tungsten slide film. Slides were digitally transposed and then compiled to generate individual plates (FIGS. 1–14).

Each plate shows the unprocessed contaminant (Not Processed); the contaminant processed according to the modified CB-18 procedure of Example 1 described above (NALC/CB-18); the contaminant treated with LZCT only as described above (LZCT); and the contaminant processed according to the modified LZCT/CB-18 procedure of Example 5 described above (LZCT/CB-18).

FIG. 1 shows the processing series using a Candida species (e.g., a yeast). The contaminant was derived from a respiratory specimen that had been processed with 0.5% NALC/3% NaOH (Kent, P. T. et al., "Public Health Mycobacteriology" in *A Guide for the Level III Laboratory*, U.S. Department of Health and Human Services, Centers for Disease Control (1985), 31–46) and had broken through the 12B/PANTA culture system. This isolate was removed from a blood-agar plate and cultivated on Sabouraud dextrose agar (Becton Dickinson, Cockeysville, Md.). There appeared to be very little difference between the unprocessed yeast (FIG. 1A) and the yeast treated with the NALC/CB-18 procedure (FIG. 1B). Treatment with the enzyme alone, however, appeared to significantly impact the staining characteristics of the yeast (FIG. 1C). When both treatments were combined (e.g., LZCT/CB-18), ghosts were readily apparent (FIG. 1D). The lines appearing in FIG. 1D were very common, and it is assumed that these were due to the release of chromosomal DNA resulting from cellular lysis. Combinations of zymolyase and Trichoderna extract were seen to be most useful in that neither alone seemed to be effective on all isolates tested.

FIGS. 2 and 3 show the processing series using molds (e.g., fungi). FIG. 2 used a mold identified only as a "soil saprophyte". This specimen was obtained from foot tissue and was cultured on potato flake agar (Becton Dickinson, Cockeysville, Md.). FIG. 3 used an Aspergillus species derived from a podiatric specimen cultured on potato flake agar. Both unprocessed molds showed dramatic mycelium and hyphae formation, as well as clearly defined conidia (FIGS. 2A and 3A). A pycnidium, or conidiomata, is clearly visible in the soil saprophyte sample (FIG. 2A). Treatment with either NALC/CB-18 (FIGS. 2B and 3B) or LZCT (FIGS. 2C and 3C) dramatically affected the mycelium integrity but neither treatment alone seemed to affect the structural integrity of the conidia. Treatment with the combination of the LZCT enzyme cocktail and CB-18 appeared to completely destroy all structural components (FIGS. 2D and 3D).

FIGS. 4, 5, 6 and 7 examine the methods of the invention on gram positive contaminants. FIG. 4 used a control *Staphylococcus aureus* isolate (ATCC 25923). FIG. 5 utilized a *Staphylococcus epidernidis* isolate derived from a respiratory specimen. FIG. 6 examined a control *Micrococcus luteus* isolate (ATCC 49732), and FIG. 7 tested a Bacillus species derived from a respiratory specimen. All strains were cultured on blood agar (Becton Dickinson, Cockeysville, Md.). All test contaminants showed clearly definable morphology in the control (FIGS. 4A, 5A, 6A and 7A). Treatment with the NALC/CB-18 procedure appeared to have minimal, if any, effect on morphology (FIGS. 4B, 5B, 6B, and 7B). Treatment of most gram positives with LZCT alone appeared to dramatically affect morphology (FIGS. 4C, 5C and 6C). The Bacillus species (FIG. 7C) appeared to be the exception, however, even the Bacillus appeared to show an impact on staining characteristics with LZCT alone. The combination of treating with lytic enzymes and CB-18 was again superior (FIGS. 4D, 5D, 6D and 7D). The mesh-like appearance of *Micrococcus luteus* when treated with LZCT/CB-18 (FIG. 6D) was again probably due to the release of chromosomal DNA. Addition of the Cytophaga extract was necessary to affect the integrity of the Bacillus.

FIGS. 8 and 9 examine the methods of the invention on gram negative contaminants. FIG. 8 used a *Klebsiella pneumoniae* isolate (ATCC 33495), and FIG. 9 utilized *Escherichia coli* (ATCC 25922). All isolates were cultured on blood agar plates. Gram negative contaminants were more difficult to visualize due to their smaller size and non-staining character. Distinct morphology can be seen in the unprocessed controls (FIGS. 8A and 9A). Treatment with the NALC/CB-18 procedure appeared to have a minimal effect on the morphology of Klebsiella (FIG. 8B), but some effect on *E. coli* (FIG. 9B). Interestingly, treatment of gram negative isolates with LZCT alone appeared to have little effect on morphology (FIGS. 8C and 9C). The combination of treating with LZCT and CB-18 was again superior (FIGS. 8D and 9D), however, some clearly definable cells were still present in the Klebsiella sample (FIG. 8D). Of these two isolates *E. coli* was, as expected, to be more fragile. Addition of the Cytophaga extract was again necessary to achieve an effect on the integrity of many of these gram negatives. Some gram negative organisms, such as *Pseudomonas aeruginosa* for example, were not affected by treatment with LZCT. Incorporation of additional enzymes, such as the Micromonospora extract (Suzuki et al., *Agric. Biol. Chem.* 49:1719–1726 (1985)), for example, would probably be required to affect Pseudomonas species.

In an attempt to show that the procedure of Example 5 was applicable to authentic clinical specimens, respiratory samples submitted to the TB-lab in Baltimore were screened for contaminants. It is important to recognize that most specimens have very low levels of contaminants, at least too low to be of any value in assessing the efficacy of the methods of the invention by microscopy. Specimens were therefore screened prospectively. For example, a portion of a given specimen was first processed by the standard NALC/NaOH procedure of Kent, P. T. et al., "Public Health Mycobacteriology" in *A Guide for the Level III Laboratory*, U.S. Department of Health and Human Services, Centers for Disease Control (1985), 31–46 and subjected to acid fast staining and microscopic analysis. A small portion (e.g., 1–2 mls) of the discarded, unprocessed specimens that presented with high levels of cellular debris were further subjected to modified procedures of Examples 1 and 5 as described below. FIGS. 10 and 11 show two clinical specimens in which the NALC/CB-18 method was compared with the LZCT/CB-18 method.

The remainder of each specimen was split equally and processed as follows. An equal volume (e.g., 1–2 mls) of either 0.5% NALC liquefaction solution (0.5% NALC, 1.45% citrate) or LZCT (LZCT=50 mM Tris-HCl, 12.5 mM citrate pH 7.6, 3 mM NaCl, 30 mM NALC, 1 mg/ml lysozyme, 500 units/ml zymolyase, 0.1 mg/ml Cytophaga extract, and 1 mg/ml Trichoderma extract) was added to the appropriate sample and incubated at 37° C. for 20 minutes with shaking (140 rpm). Both tubes were brought to 9 mls with sterile filtered water and then brought to a final volume of 10 mls with 1 ml of 10× CB-18 (10× CB-18=10 mM CB-18, 500 mM Tris-HCl pH 8.0, 50 mM NALC, 1 mM NaCl). Both tubes were then incubated at 37° C. for 90 minutes with shaking (140 rpm). Following this incubation 30 μl aliquots were taken for microscopic analysis and photographed as described above.

Figure 10A:
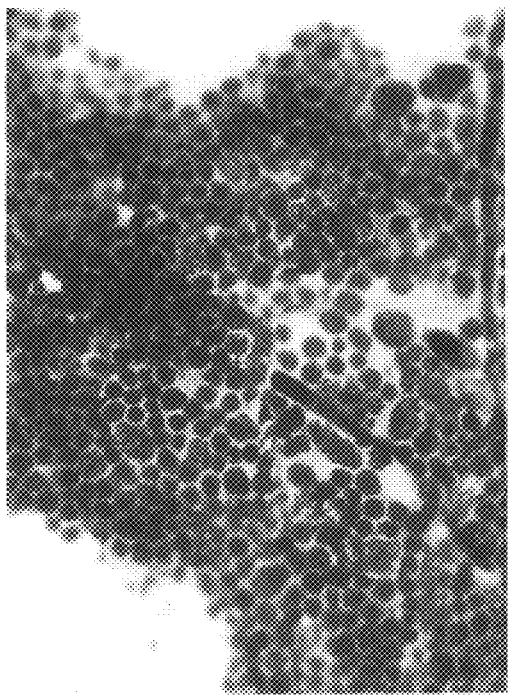
FIG. 10(A, B) is a series of photomicrographs that show the contaminant results obtained using different processing conditions and an authentic clinical specimen heavily contaminated with yeast. These conditions include either treating the specimen with CB-18 as described in Example 1 (A), or treating the specimen first with LZCT and then CB-18, as described in Example 6 (B).
Figure 10B:
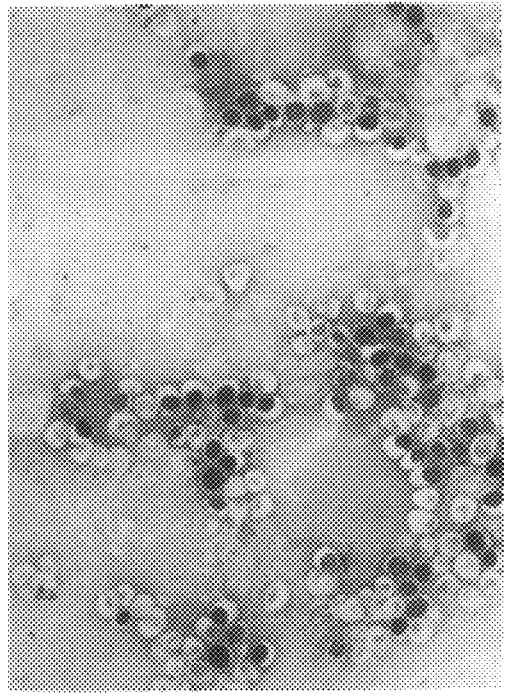

FIG. 10 shows a clinical specimen heavily contaminated with yeast. Based on the comparison of FIGS. 1A and 1B it is assumed that the yeast in FIG. 10A looked similar to the unprocessed organism. Regardless, the comparative NALC/CB-18 slides (FIGS. 1B and 10A) appeared similar. Processing with the LZCT/CB-18 procedure again produced dramatic changes in staining (FIG. 10B). Ghosts were again present in the LZCT/CB-18 processed specimen (FIG. 10B).

Figure 11A:
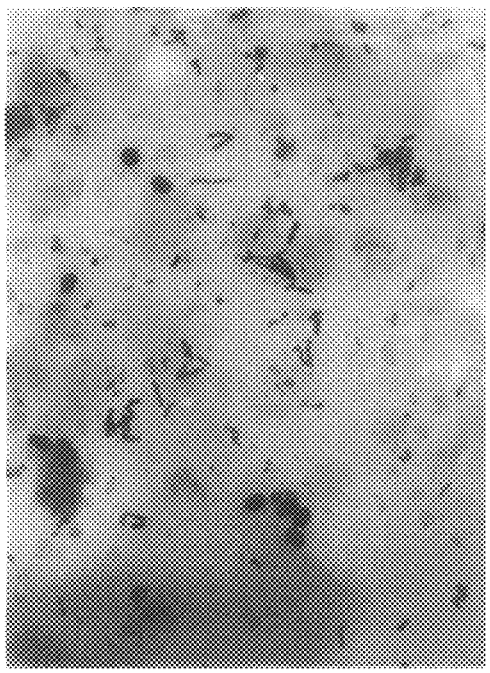
FIG. 11(A, B) is a series of photomicrographs that show the contaminant results obtained using different processing conditions and a second authentic clinical specimen with a mixed infection. These conditions include either treating the specimen with CB-18 as described in Example 1 (A), or treating the specimen first with LZCT and then CB-18, as described in Example 6 (B).
Figure 11B:
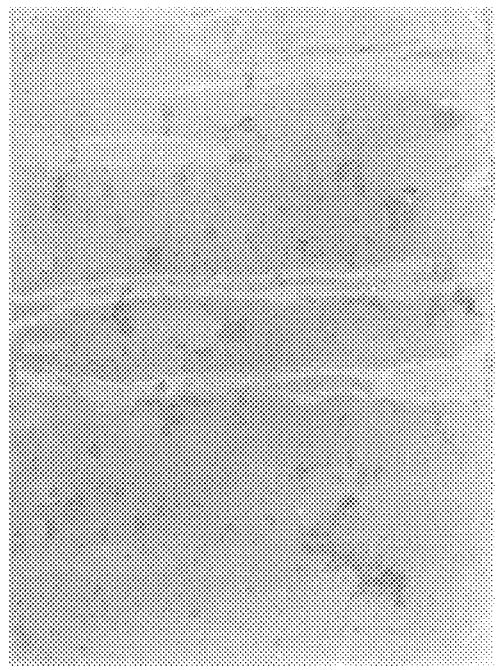

FIG. 11 shows a specimen with a mixed infection. In this example the specimen had a much lower concentration of yeast, but also contained what appeared to be gram positive rods (FIG. 11A). Epithelial cells also appeared to survive the NALC/CB-18 treatment FIG. 11A: blotches). Treatment with LZCT, however, left no discernible morphology (FIG. 11B). Most of the slide used to generate FIG. 11B had low levels of debris. The photograph in FIG. 11B actually represented a concentrated debris field.

Combining an enzyme cocktail with CB-18 processing (e.g., WO 95/27076) clearly affected the integrity of contaminants. Similar experiments testing several mycobacteria showed that the LZCT cocktail was impotent in this capacity. While the LZCT/CB-18 procedure may not actually be lysing contaminants, it clearly affected structural integrity. For example, actual lysing may be an artifact of the staining procedure itself: The cells may be whole when applied to the slide, but were actually disrupted when treated with the staining reagents (e.g. iodine and/or alcohol). Regardless, the structural integrity of these contaminants was dramatically affected as evidenced by the microscopic results.

In conclusion, while it may be true that cells were not being completely lysed by the lytic enzymes, those cells that were not lysed were left fragile and defective. As such they are expected to be more susceptible to the action of mechanical disruption (for example, sonication), the detergent (e.g., CB-18) and/or the antibiotics (e.g., PANTA (Becton Dickinson, Cockeysville, Md.), PVNA (DIFCO Laboratories, Detroit, Mich.) or MAS (Organon Teknika, Durham, N.C.)).

Example 7

The Reverse Procedure: Digesdon with Lytic Enzymes Following Processing with Betaine-Like Detergents A second preferred embodiment involves first processing clinical specimens with a betaine-like detergent according to WO 95/27076 (e.g., CB-18) and then treating with the lytic enzyme cocktail to facilitate destabilizing the structural integrity of contaminants. This embodiment is essentially the reverse of the procedure described in Examples 5, wherein the procedure of Example 1 (e.g., NALC/CB-18) precedes digestion with lytic enzymes. The procedure described below is not intended to be limiting of the invention, but is one example of how this embodiment might be accomplished.

(1) Place 1–10 mls of specimen in a 50 ml conical tube. NOTE: While respiratory specimens are the predominant specimen type expected to be used in conjunction with the procedure described here, other specimen types such water, soil, tissue, fecal and other specimens can be adapted for use in conjunction with the procedure below. Some of these specimens might first be clarified by resuspending in water or buffer and passing the mixture over a Spin-X II column fitted with a 20–60 micron flit (Corning Costar, Boston, Mass.). Any specimen could then be treated as described below.

(2) To the specimen add an equal volume of 0.5% NALC liquefaction solution (0.5% NALC/25 mM sodium citrate) and vortex well.

(3) Incubate at room temperature for 10 minutes (vortex at about 5 minutes, and then just before the next step).

(4) Open the tube and add sterile, filtered water to the specimen to a final volume of approximately 35 mls.

(5) Add 4 mls of 10× CB-18 Buffer (e.g., 10×=10 mM CB-18, 0.5 M Tris-HCl pH 8.0, 50 mM NALC, 1 mM NaCl).

(6) Vortex well to completely mix the specimen.

(7) Incubate at 37° C. for 90 minutes with shaking (140 rpm).

(8) Vortex and then centrifuge specimens at 4,000×g for 20 minutes at 30° C.

(9) Decant the tubes completely and add 0.5–1 ml of sterile water or buffer to the specimen.

(10) Resuspend the pellet completely and add an equal volume of 2×-lytic enzyme decontamination solution (e.g., 1×-LZCT=50 mM Tris-HCl, 12.5 mM citrate pH 7.6, 3 mM NaCl, 30 mM NALC, 1 mg/ml lysozyme, 500 units/ml zymolyase, 0.1 mg/ml Cytophaga extract, and 1 mg/ml Trichoderma extract) and vortex well.

(11) Incubate for approximately 10 minutes at 37° C. with gentle shaking. (This step may require up to 60 minutes to achieve maximal lysis. Incubation might also be accomplished at room temperature.)

NOTE: At this point in the procedure an aliquot might be taken for detection, such as by nucleic acids amplification for example, or further processed as described below.

(12) Open the tube and add sterile, filtered water to the specimen to a final volume of approximately 35 mls.

(13) Add 4 mls of 10× CB-18 Buffer (10×=10 mM CB-18, 0.5 M Tris-HCl pH 8.0, 50 mM NALC, 1 mM NaCl).

(14) Vortex well to completely mix the specimen and immediately subject the specimen to centrifugation at 4,000×g for 20 minutes at 30° C.

(15) Decant the tubes completely and add 500 µl of sterile water or buffer to the specimen.

(16) Resuspend the pellet completely and prepare the sediment for detection such as by nucleic acids amplification, culture or immunodiagnostic techniques.

Example 8

The Reverse Procedure: Digesting Specimens with LZCT Following CB-18 Processing

The second preferred embodiment, outlined in Example 7, was used below to digest specimens with the LZCT enzyme cocktail described in Example 5 after first having been processed by the NALC/CB-18 procedure described in Example 1. The CB-18 components used below were described in Example 1, and the LZCT components employed were described in Example 5.

Prospective contaminants were purified, identified by standard techniques, and grown on the appropriate culture media. Replicate tubes were manufactured as described in Example 6.

For each isolate four replicates were started as follows. The first replicate was unprocessed ("Not Processed"), the second replicate was treated with the a modified version of the standard NALC/CB-18 procedure of WO 95/27076 as described in Example 1 ("NALC/CB-18"). The third replicate was first treated with LZCT and then CB-18 according to a modified procedure of that described in Example 5 ("LZCT➡CB-18"). The fourth replicate was first processed with a modified version of the standard NALC/CB-18 procedure of WO 95/27076 as described in Example 1, and then treated with LZCT according to a modified procedure of that described in Example 7 ("CB-18➡LZCT").

The unprocessed tube was brought to 10 mls with sterile, filtered water, mixed and 30 µl aliquots taken for microscopic analysis and photography as described above. The procedures used to process the remaining tubes were modified as follows. An equal volume (e.g., 2 mls) of 0.5% NALC liquefaction solution was added to the NALC/CB-18 and CB-18➡LZCT tubes, and an equal volume of the 2× LZCT enzyme cocktail (1× LZCT=50 mM Tris-HCl, 12.5 mM citrate pH 7.6, 3 mM NaCl, 30 mM NALC, 1 mg/ml lysozyme, 500 units/ml zymolyase, 0.1 mg/ml Cytophaga extract, and 1 mg/ml Trichoderma extract) was added to the LZCT➡CB-18 specimen. All tubes were incubated at 37° C. for 20 minutes with shaking (140 rpm). All tubes were then brought to a final volume of approximately 35 mls with sterile filtered water, and then brought to 40 mls with 4 ml of 10× CB-18 (10× CB-18=10 mM CB-18, 500 mM Tris-HCl pH 8.0, 50 mM NALC, 1 mM NaCl). All tubes were incubated at 37° C. for 90 minutes with shaking (140 rpm), and subjected to centrifugation at 4,000×g for 20 minutes at 30° C. Specimens were decanted and then resuspended in either 1 ml of sterile filtered water (e.g., the NALC/CB-18 and LZCT➡CB-18 tubes), or 1 ml of 2× LZCT enzyme decontamination solution (e.g., the CB-18➡LZCT tube) (1×

LZCT=50 mM Tris-HCl, 12.5 mM citrate pH 7.6, 3 mM NaCl, 30 mM NALC, 1 mg/ml lysozyme, 500 units/ml zymolyase, 0.1 mg/ml Cytophaga extract, and 1 mg/ml Trichoderma extract). The tubes were incubated at room temperature for 5 minutes before 30 µl aliquots were taken for microscopic analysis and photography as described above.

Figure 12A:
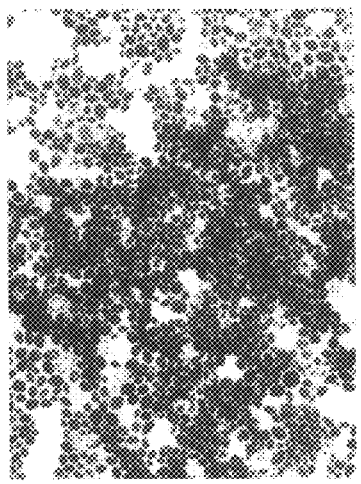
FIG. 12(A, B, C) is a series of photomicrographs that show the contaminant results obtained using different processing conditions and a Candida isolate as a prototype yeast contaminant. These conditions include cells treated with CB-18 as described in Example 1 (A); cells treated with the LZCT lytic enzyme formulation, and then with CB-18 as described in Example 6 (B); and cells treated first with CB-18 and then with LZCT as described in Example 8 (C).
Figure 12B:
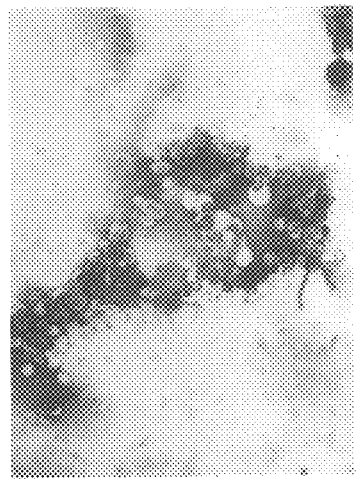
Figure 12C:

FIG. 12 shows the processing series using the Candida species (e.g., a yeast) described in Example 6, FIG. 1. The unprocessed yeast was omitted from this series as it appeared identical to that in FIG. 1A, but the NALC/CB-18 specimen was included for reference (e.g., compare FIGS. 1B and 12A). When both treatments were combined (e.g., LZCT➞CB-18), ghosts were again readily apparent (compare FIGS. 1D and 12B). When the specimen was first processed with CB-18, as described in Example 1, and then treated with the LZCT lytic enzyme cocktail according to the modified procedure of Example 7 (e.g., CB-18➞LZCT), the results were dramatic (FIG. 12C). Very little discernible morphology was apparent on the slide.

Figure 13A:
FIG. 13(A, B, C) is a series of photomicrographs that show the contaminant results obtained using different processing conditions and a Bacillus species as a prototype gram positive rod contaminant. These conditions include cells treated with CB-18 as described in Example 1 (A); cells treated with the LZCT lytic enzyme formulation, and then with CB-18 as described in Example 6 (B); and cells treated first with CB-18 and then with LZCT as described in Example 8 (C).
Figure 13B:
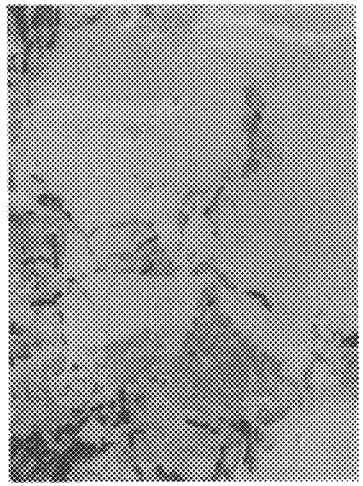
Figure 13C:
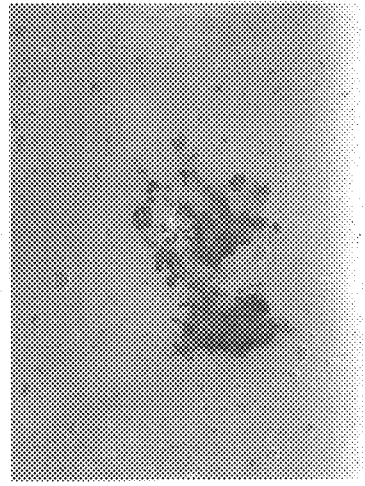

FIG. 13 examined the methods of the invention, as outlined in Example 7, on a gram positive contaminant; the same Bacillus species described in Example 6, FIG. 7. The unprocessed Bacillus was omitted from this series (see FIG. 7A), but the NALC/CB-18 specimen was again included for reference (compare FIGS. 7B and 13A). When the modified embodiment of Example 5 (e.g., LZCT➞CB-18) was employed in this experiment, significant changes in staining were again observed but morphology was still readily apparent (compare FIGS. 7D and 13B). When the specimen was first processed with CB-18 and then treated with LZCT the results were again dramatic (FIG. 13C). Again, very little observable morphology was apparent, just large debris fields.

FIG. 14 examined the methods of the invention on another common gram negative respiratory contaminant, *Proteus mirabilis* (ATCC 12453). The Proteus was also cultured on blood agar. Again, gram negative contaminants were more difficult to visualize due to their smaller size and non-staining character. The unprocessed control (FIG. 14A) was included to show the distinct morphology of the untreated organism. The Proteus appeared to behave similar to the Klebsiella of FIG. 8. For example, treatment with the NALC/CB-18 procedure appeared to have a minimal effect on structural integrity (compare FIGS. 8B and 14B), and both the Proteus (FIG. 14C) and Klebsiella (FIG. 8D) were destabilized, but not completely destroyed by the LZCT/CB-18 procedure. This is in contrast to the *E. coli* of FIG. 9D in which morphology was almost completely absent. As with FIG. 12C and 13C, the reverse procedure (e.g., CB-18➞LZCT) appeared to be the most effective treatment to eliminate morphology (FIG. 14D).

The procedure of Example 7 is probably lysing some contaminants. Those that are not lysed are probably left even more fragile and defective than contaminants processed using the procedure of Example 5, and as such are expected to be even more susceptible to mechanical disruption (for example, sonication) or to the action of antibiotics such as PANTA (Becton Dickinson, Cockeysville, Md.), PVNA (DIFCO Laboratories, Detroit, Mich.) or MAS (Organon Teknika, Durham, N.C.), or other formulations. While there are more steps in the embodiment of Example 7 relative to the embodiment of Example 5, the former may provide significant advantages when heavily contaminated specimens are being processed (e.g., sputa, soil and fecal samples). More efficient elimination of contaminants would certainly improve methods of detection by culture, and eliminating heterologous nucleic acids, nucleases, and/or proteases during processing would also improve the efficiency of amplification.

In conclusion, the second embodiment, the "reverse procedure" (e.g., CB-18➞LZCT), appeared to be the most effective means at destabilizing the structural integrity of the contaminants. It is clear that the enzymes are not only active in the presence of residual amounts of CB-18, but may also be more efficient. If CB-18 were stripping peripherally associated cell wall constituents, then it would make sense that the integral structural components would be more susceptible to enzymatic digestion. In addition, liquefaction of the specimen most likely facilitates exposure of the capsules of the contaminants.

Example 9

Studies Processing Clinical Specimens with the CB-8/LZCT Procedure

A modified version of the procedure described in Example 7 was used to process clinical specimens. Two hundred forty (240) discarded respiratory specimens from both the microbiology (n=194) and TB (n=46) laboratories at Quest Diagnostics-Baltimore were collected at random. The specimens were first mixed with an equal volume of 0.5% NALC, incubated at room temperature for 10 minutes and then brought to 35 mls with sterile filtered water. Specimens were then mixed with 4 mls of 10× CB-18 (10× CB-18=10 mM CB-18, 500 mM Tris-HCl pH 8.0, 50mM NALC, 1 mM NaCl), incubated for 90 minutes at 37° C. with shaking (140 rpm), and then subjected to centrifugation at 4,000×g for 20 minutes at 30° C. Following centrifugation specimens were decanted and sediments re-suspended in 500 µl of sterile filtered water. A portion of the re-suspended sediment (250 µl) was then mixed with an equal volume of 2× LZCT (1× LZCT=50 mM Tris-HCl, 12.5 mM citrate pH 7.6, 3 mM NaCl, 30 mM NALC, 1 mg/ml lysozyme, 500 units/ml zymolyase, 0.1 mg/ml Cytophaga extract, and 1 mg/ml Trichoderma extract) and incubated for 20 minutes at 37° C. Most specimens (200 of 240) were re-suspended in 2× LZCT containing 0.15% lecithin (lecithin (Sigma, St. Louis, Mo.: Cat. # P 5394) was made up as a 100× concentrate in 100% ethanol (3 grams in 40 mls) and diluted in the 2× LZCT buffer immediately prior to use)). Decontaminated sediments were planted on BACTEC 12B liquid media supplemented with PANTA (Becton Dickinson, Cockeysville, Md.) which had been fortified with ceftazidime (8 µg/ml final: the induced susceptibility caused by CB-18, as described in Example 4, can be overcome by the addition of lecithin. During the course of this study 8 sterility blanks were run (e.g., sterile water processed as above with CB-18 and then incubated with LZCT and planted in 12B/PANTA/caz). Bottles were checked every other day for the first two weeks and then weekly for the next four weeks. Portions of positive bottles were analyzed by acid fast staining (Kent, P. T. et al., "Public Health Mycobacteriology," in *A Guide for the Level III Laboratory*, U.S. Department of Health and Human Service, Centers for Disease Control, (1985) pp. 57–70) and sub-cultured on blood agar plates. Contaminants growing on blood agar plates were identified by morphology and/or gram stain and then differentiated as either oxidase/catalase, positive or negative. Contaminants were then speciated, and antibiotic sensitivities determined, using MicroScan panels (Dade International, Sacramento, Calif.). The results of this study are presented in Table 7.

TABLE 7

CB-18/LZCT Processing Contaminants
(n = 240)

| | Micro Lab (n = 194) | | AFB Lab (n = 46) | | Total | |
|---|---|---|---|---|---|---|
| Isolate Type | # | % | # | % | # | % |
| Gram Negative | 30 | 73.2% | 2 | 100% | 32 | 74.4% |
| Gram Positive | 10 | 24.4% | 0 | — | 10 | 23.2% |
| Yeast | 1 | 2.4% | 0 | — | 1 | 2.3% |
| Fungi | 0 | — | 0 | — | 0 | — |
| Total # Isolates: | 41 | | 2 | | 43 | |
| Total # Spec. | 36/194 | | 2/46 | | 38/240 | |
| Contam. Rate | 18.5% | | 4.3% | | 15.8% | |

The results presented in Table 7 showed that the contamination rate for all specimens was 15.8%. Among specimens from the micro-lab the contamination rate was 18.5%, but only 4.3% for specimens from the TB-lab. Analysis of contaminants from the micro-lab revealed that 73.2% of the isolates were gram negative, 24.4% were gram positive, and 2.4% were yeast. Further examination of the gram negative isolates revealed the following distribution: Pseudomonas species (n=13), *Providencia stuartii* (n=7), *Alcaligenes xylosoxidans* (n=4), *Serratia marcescens* (n=3), *Morganella morgani* (n=2) and *Acinetobacter lwoffii* (n=1). Among the gram positive isolates, there were 8 Staphylococcus species, 1 Bacillus species, and 1 diphtheroid. The two contaminants from the TB -lab were *Pseudomonas aeruginosa* and *Alcaligenes xylosoxidans*. Of the 8 sterility blanks, none became positive.

The results presented in Table 7 suggest that the CB-18/LZCT procedure had little, if any, impact on the contamination rate from specimens derived from the micro-lab, but a dramatic impact on the contamination rate from specimens derived from the TB-lab. Based on the argument presented in Example 2, this was the expected result. For example, the primary contaminant type seen from the micro-lab was gram negative (Table 3), whereas the primary contaminant type from the TB-lab was mycologic (Tables 4 and 5). The LZCT enzyme cocktail employed was specifically designed to minimize mycologic contaminants (FIGS. 1–3, and 10–12), affect the integrity of gram positive contaminants to some degree (FIGS. 4–7, and 13), and impact gram negative contamination but to a much lesser degree (FIGS. 8, 9 and 14). The LZCT formulation was extremely efficient at eliminating almost all mycologic contaminants, many gram positive contaminants, but only a few gram negative contaminants. Therefore, the overall contamination rate among specimens from the micro-lab would be affected only to a minor degree, but the contamination rate among specimens from the TB-lab would be significantly impacted.

Based on the above discussion the results seen in Table 7 for the Baltimore TB-lab could have been predicted from the results in Table 5. For example, if all mycologic contaminants were removed from Table 5 (contaminants in the CB-18 Pilot Study that were derived from the Baltimore TB-lab), the contamination rate would drop to approximately 8.8%. Eliminating most gram positive and a few gram negative contaminants from this same group would bring the contamination rate in-line with that observed in Table 7. Incorporation of a sonication step (for example, at 35 kHz) or enzymes that affect gram negative bacteria are additional embodiments of the invention herein.

In the embodiment used in the study of Table 7, it is expected that active enzymes are added to the 12B culture bottles. In several instances, it was observed that the growth index (GI) became positive (15<GI<100) and then returned to baseline (GI=0). This was not observed with the standard 12B/PANTA/caz system. This phenomenon was attributed to such enzymatic activity in the culture bottle, and may be an advantage of this embodiment. As such, bottles should not be re-digested or analyzed until the GI>100.

Having now fully described the invention, it will be understood by those with skill in the art that the invention may be performed within a wide and equivalent range of conditions, parameters and the like, without affecting the spirit or scope of the invention or any embodiment thereof.

What is claimed is:

1. A method of preparing a sample suspected of containing a microorganism having mycolic acid structures in its outer membrane for determination of the presence of said microorganism, said method comprising:
   a. treating a specimen or extract thereof by contacting a composition comprising one or more lytic enzymes that are active against gram positive bacteria, gram negative bacteria, or mycologic organisms with said sample; wherein said treating selectively lowers or eliminates levels of microorganisms in the specimen or extract thereof that do not contain mycolic acid structures in their outer membranes relative to the level of microorganisms in said specimen or extract thereof that do contain mycolic acid structures in their outer membrane, wherein said microorganisms containing mycolic acid structures in their outer membrane retain viability after said treating and,
   b. obtaining or deriving said sample for said determination from the treated specimen or extract thereof of part (a).

2. The method of claim 1, wherein at least one said lytic enzyme in said composition is selected from the group consisting of an agarase, amidase, aminidase, arabinosidase, cellulase, chitinase, dextranase, dextrinase, fructofuranosidase, fructosidase, fucoidanase, fucosidase, furanosidase, galactanase, galactosidase, galacturonase, galacturonosidase, glucanase, glucosidase, glucanohydrolase, glucohydrolase, glucuronidase, glycanase, glycosidase, laminarinase, lichenase, mannanase, mannosidase, pectinase, peptidase, polysaccharase, protease, proteinase, pullulanase, rhamnosidase, trehalase, xylanase, and xylosidase.

3. The method of claim 2, wherein said lytic enzyme is an agarase.

4. The method of claim 2, wherein said lytic enzyme is an amidase.

5. The method of claim 4, wherein said amidase is a peptidase, protease or proteinase.

6. The method of claim 5, wherein said amidase is a peptidase.

7. The method of claim 6, wherein said peptidase is achromopeptidase.

8. The method of claim 2, wherein said lytic enzyme is an aminidase.

9. The method of claim 8, wherein said aminidase is an endo-$\beta$-1,4-N-acetylhexosaminidase or a muraminidase.

10. The method of claim 8, wherein said aminidase is lysozyme.

11. The method of claim 2, wherein said lytic enzyme is an arabinosidase.

12. The method of claim 2, wherein said lytic enzyme is a cellulase.

13. The method of claim 2, wherein said lytic enzyme is a chitinase.

14. The method of claim 2, wherein said lytic enzyme is a dextranase.

15. The method of claim 2, wherein said lytic enzyme is a dextrinase.

16. The method of claim 2, wherein said lytic enzyme is a fructofuranosidase.

17. The method of claim 2, wherein said lytic enzyme is a fructosidase.

18. The method of claim 2, wherein said lytic enzyme is a fucoidanase.

19. The method of claim 2, wherein said lytic enzyme is a fucosidase.

20. The method of claim 2, wherein said lytic enzyme is a furanosidase.

21. The method of claim 2, wherein said lytic enzyme is a galactanase.

22. The method of claim 2, wherein said lytic enzyme is a galactosidase.

23. The method of claim 2, wherein said lytic enzyme is a galacturonase.

24. The method of claim 2, wherein said lytic enzyme is a galacturonosidase.

25. The method of claim 2, wherein said lytic enzyme is a glucanase.

26. The method of claim 2, wherein said lytic enzyme is an glucosidase.

27. The method of claim 2, wherein said lytic enzyme is a glucanohydrolase.

28. The method of claim 2, wherein said lytic enzyme is a glucohydrolase.

29. The method of claim 2, wherein said lytic enzyme is a glucuronidase.

30. The method of claim 2, wherein said lytic enzyme is a glycanase.

31. The method of claim 2, wherein said lytic enzyme is a glycosidase.

32. The method of claim 2, wherein said lytic enzyme is a laminarinase.

33. The method of claim 2, wherein said lytic enzyme is a lichenase.

34. The method of claim 2, wherein said lytic enzyme is a mannanase.

35. The method of claim 2, wherein said lytic enzyme is a mannosidase.

36. The method of claim 2, wherein said lytic enzyme is a pectinase.

37. The method of claim 2, wherein said lytic enzyme is a polysaccharase.

38. The method of claim 2, wherein said lytic enzyme is a pullanase.

39. The method of claim 2, wherein said lytic enzyme is a rhamnosidase.

40. The method of claim 2, wherein said lytic enzyme is a trehalase.

41. The method of claim 2, wherein said lytic enzyme is a xylanase.

42. The method of claim 2, wherein said lytic enzyme is a xylosidase.

43. The method of claim 1, wherein said lytic enzymes comprise lyticase.

44. The method of claim 1, wherein said lytic enzymes comprise mutanolysin.

45. The method of claim 1, wherein said lytic enzymes comprise lysostaphin.

46. The method of claim 1, wherein said lytic enzymes comprise at least one said lytic enzyme in said composition that is a Achromobacter, Arthrobacter, Aspergillus, Bacillus, Brevibacterium, Cytophaga, Flavobacterium, Micromonospora, Oerskovia, Penicillium, Rhizoctonia, Staphylococcus, Streptomyces, or Trichoderma lytic enzyme.

47. The method of claim 46, wherein said lytic enzymes comprise a Achromobacter lytic enzyme.

48. The method of claim 46, wherein said lytic enzymes comprise a Arthrobacter lytic enzyme.

49. The method of claim 46, wherein said lytic enzymes comprise an Aspergillus lytic enzyme.

50. The method of claim 46, wherein said lytic enzymes comprise a Bacillus lytic enzyme.

51. The method of claim 46, wherein said lytic enzymes comprise a Brevibacterium lytic enzyme.

52. The method of claim 46, wherein said lytic enzymes comprise a Cytophaga lytic enzyme.

53. The method of claim 46, wherein said lytic enzymes comprise a Flavobacterium lytic enzyme.

54. The method of claim 46, wherein said lytic enzymes comprise a Micromonospora lytic enzyme.

55. The method of claim 46, wherein said lytic enzymes comprise a Oerskovia lytic enzyme.

56. The method of claim 46, wherein said lytic enzymes comprise a Penicillium lytic enzyme.

57. The method of claim 46, wherein said lytic enzymes comprise a Rhizoctonia lytic enzyme.

58. The method of claim 46, wherein said lytic enzymes comprise a Staphylococcus lytic enzyme.

59. The method of claim 46, wherein said lytic enzymes comprise a Streptomyces lytic enzyme.

60. The method of claim 46, wherein said lytic enzymes comprise a Trichodevma lytic enzyme.

61. The method of claim 46, wherein said lytic enzymes comprise both a Trichoderma and a Cytophaga lytic enzyme.

62. The method of claim 1, wherein said lytic enzymes comprise lysozyme, lyticase, Trichoderma, and Cytophaga lytic enzymes.

63. The method of claim 1, wherein said lytic enzymes comprise lysozyme, lyticase, Trichodevma, Cytophaga, and Micromonospora lytic enzymes.

64. The method of claim 1, wherein said method further comprises the addition of a reducing agent before, during and/or after the addition of said one or more lytic enzymes.

65. The method of claim 64, wherein said addition of said reducing agent is before the addition of said one or more lytic enzymes.

66. The method of claim 64, wherein said addition of said reducing agent is during said addition of said one or more lytic enzymes.

67. The method of claim 64, wherein said addition of said reducing agent is after the addition of said one or more lytic enzymes.

68. The method of claim 1, wherein said method further comprises the addition of a betaine-like detergent before, during and/or after the addition of said one or more lytic enzymes.

69. The method of claim 68, wherein said addition of said betaine-like detergent is before said addition of said one or more lytic enzymes.

70. The method of claim 68, wherein said addition of said betaine-like detergent is during said addition of said one or more lytic enzymes.

71. The method of claim 68, wherein said addition of said betaine-like detergent is after said addition of said one or more lytic enzymes.

72. The method of claim 67, wherein said composition comprising one or more lytic enzymes also contains phospholipids.

73. The method of claim 72, wherein said phospholipid is phophatidylcholine.

74. The method of claim 68, wherein said betaine-like detergent is selected from the group consisting of CB-like, SB-like, HSB-like, PB-like, StB-like, PhB-ike, SoB-like, RevB-like, AO-like, cAB-like, and ImB-like detergents.

75. The method of claim 74, wherein said betaine-like detergent is a CB-like detergent.

76. The method of claim 75, wherein said CB-like detergent has the structure

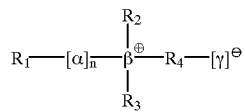

wherein $R_1$ is $C_8$–$C_{22}$;
α is —$CH_2$—, —CH(OH)—, —(CO)—NH—$CH_2CH_2CH_2$—, —O—, or —C(O)—;
n is 0 or 1;
β is —N⊕—, —P⊕—, or —S⊕—;
$R_2$ is —H, —$CH_3$, —$C_2H_5$, —$C_3H_7$, or —$C_4H_9$;
$R_3$ is —H, —$CH_3$, —$C_2H_5$, —$C_{31}H_7$, or —$C_4H_9$;
$R_4$ is —$CH_2$—, —$C_2H_4$—, —$C_3H_6$—, —$C_4H_8$— $C_5H_{10}$—, —$C_6H_{12}$—, —$CH_2$—$C_6H_4$—, —$C_mH_{2m}$—, —CH(OH)$CH_2CH_2$—, —$CH_2$CH(OH)$CH_2$—, or —$C_mH_{2m-1}$(OH)— where m is $\geq$1; and
γ is —COO⊖.

77. The method of claim 76, wherein said CB-like detergent is selected from the group consisting of N-(carboxymethyl)-N,N-dimethyl-1-hexadecanaminium, inner salt (CAS® No. 693-33-4),
cococarboxymethylbetaine and (CAS® No. 68424-94-2),
N-(carboxymethyl)-N,N-dimethyl-9-octadecen-1-aminium, inner salt (CAS® No. 871-37-4),
N-(carboxymethyl)-N,N-dimethyl-3-((1-oxooctadecyl)amino)-1-propanaminium, inner salt (CAS® No. 6179-44-8),
3-amino-N(carboxymethyl)-N,N-dimethyl-1-propanaminium N-C8-C22 acyl derivatives, inner salt (CAS® No. 84082-44-0),
N-(carboxymethyl)-3-((12-hydroxy-1-oxo-9-octadecenyl)amino)-N,N-dimethyl-1-propanaminium, inner salt (CAS® No. 71850-81-2),
cocoamidopropyl carboxymethylbetaine (CAS® No. 61789-39-7 and CAS® No. 61789-40-0),
N-(2-carboxyethyl)-N,N-dimethyl-1-dodecanaminium, inner salt (CAS® No. 16527-85-8),
N-(2-carboxyethyl)-N,N-dimethyl-1-tridecanaminium, inner salt (CAS® No. 132621-79-5),
N-(2-carboxyethyl)-N,N-dimethyl-1-tetradecanaminium, inner salt (CAS® No. 69725-38-3),
N-(2-carboxyethyl)-N,N-dimethyl-1-hexadecanaminium, inner salt (CAS® No. 42416-43-3),
N-(2-carboxyethyl)-N,N-dimethyl-1-octadecanaminium, inner salt (CAS® No. 30612-73-8),
N-dodecyl-beta-alanine (CAS® No. 1462-54-0),
N-(3-carboxypropyl)-N,N-dimethyl-1-undecanaminium, inner salt (CAS® No. 150147-53-8),
N-(3-carboxypropyl)-N,N-dimethyl-1-dodecanaminium, inner salt (CAS® No. 15163-30-1),
N-(3-carboxypropyl)-N,N-dimethyl-1-tetradecanamninium, inner salt (CAS® No. 146959-90-2),
N-(3-carboxypropyl)-N,N-dimethyl-1-pentadecanaminium, inner salt (CAS® No. 146959-91-3),
N-(3-carboxypropyl)-N,N-dimethyl-1-hexadecanaminium, inner salt (CAS® No. 71695-32-4),
N-(3-carboxypropyl)-N,N-dimethyl-1-octadecanaminium, inner salt (CAS® No. 78195-27-4),
N-(4-carboxybutyl)-N,N-dimethyl-1-dodecanaminium, inner salt (CAS® No. 120139-51-7),
N-(5-carboxypentyl)-N,N-dimethyl-1-dodecanaminium, inner salt (CAS® No. 76392-97-7),
N-(5-carboxypentyl)-N,N-dimethyl-1-hexadecanaminium, inner salt (CAS® No. 73565-98-7),
N-(6-carboxyhexyl)-N,N-dimethyl-1-dodecanaminium, inner salt (CAS® No. 132621-80-8),
4-carboxy-N-dodecyl-N,N-dimethyl-benzenemethanaminium, inner salt (CAS® No. 71695-31-3),
2-carboxy-N-dodecyl-N,N-dimethyl-benzenemethanaminium, inner salt (CAS® No. 71695-34-6),
4-carboxy-N-hexadecyl-N,N-dimethyl-benzenemethanaminium, inner salt (CAS® No. 71695-33-5),
2-carboxy-N-hexadecyl-N,N-dimethyl-benzenemethanaminium, inner salt (CAS® No. 71695-35-7),
tallow glycinate (CAS® No. 70750-46-8),
soyamidopropyl carboxymethylbetaine, and
babassuamidopropyl carboxymethylbetaine.

78. The method of claim 77, wherein said CB-like detergent is selected from the group consisting of N-(2-carboxyethyl)-N,N-dimethyl-1-dodecanaminium, inner salt (CAS® No. 16527-85-8),
N-(2-carboxyethyl)-N,N-dimethyl-1-tridecanaminium, inner salt (CAS® No. 132621-79-5),
N-(2-carboxyethyl)-N,N-dimethyl-1-tetradecanaminium, inner salt (CAS® No. 69725-38-3),
N-(2-carboxyethyl)-N,N-dimethyl-1-hexadecanaminium, inner salt (CAS® No. 42416-43-3),
N-(2-carboxyethyl)-N,N-dimethyl-1-octadecanaminium, inner salt (CAS® No. 30612-73-8),
N-(3-carboxypropyl)-N,N-dimethyl-1-undecanaminium, inner salt (CAS® No. 150147-53-8),
N-(3-carboxypropyl)-N,N-dimethyl-1-dodecanaminium, inner salt (CAS® No. 15163-30-1),
N-(3-carboxypropyl)-N,N-dimethyl-1-tetradecanaminium, inner salt (CAS® No. 146959-90-2),
N-(3-carboxypropyl)-N,N-dimethyl-1-pentadecanaminium, inner salt (CAS® No. 146959-91-3),
N-(3-carboxypropyl)-N,N-dimethyl-1-hexadecanaminium, inner salt (CAS® No. 71695-32-4),
N-(3-carboxypropyl)-N,N-dimethyl-1-octadecanaminium, inner salt (CAS® No. 78195-27-4), and
N-(4-carboxybutyl)-N,N-dimethyl-1-dodecanaminium, inner salt (CAS® No. 120139-51-7).

79. The method of claim 78, wherein said carboxybetaine is N-(3-carboxypropyl)-N,N-dimethyl-1-octadecanaminium, inner salt (CB-18) (CAS® No. 78195-27-4).

80. The method of claim 74, wherein said betaine-like detergent is an SB-like detergent.

81. The method of claim 80, wherein said SB-like detergent is selected from the group consisting of SB-18, SB-16, SB-14 and SB-12.

82. The method of claim 81, wherein said SB-like detergent is SB-16.

83. The method of claim 81, wherein said SB-like detergent is SB-18.

84. The method of claim 1, wherein said method further comprises the addition of one or more antibiotics before, during and/or after addition of said one or more lytic enzymes.

85. The method of claim 84, wherein said addition of one or more antibiotics occurs before said addition of said one or more lytic enzymes.

86. The method of claim 84, wherein said addition of one or more antibiotics occurs during said addition of said one or more lytic enzymes.

87. The method of claim 84 wherein said addition of one or more antibiotics occurs after said addition of said one or more lytic enzymes.

88. The method of claim 1, further comprising the use of mechanical disruption after the enzyme treatment.

89. The method of claim 88, wherein said mechanical disruption is sonication.

90. The method of claim 1, wherein said bacteria is a member of the mycobacteria.

91. The method of claim 90, wherein said member of said mycobacteria comprises at least one member of the *Mycobacterium tuberculosis* complex, *Mycobacterium avium* complex, *Mycobacterium kansasii*, or *Mycobacterium fortuitum* complex.

92. The method of claim 91, wherein said member of said mycobacteria comprises at least one member of the *Mycobacterium tuberculosis* complex.

93. The method of claim 91, wherein said member of said mycobacteria comprises at least one member of the *Mycobacterium avium* complex.

94. The method of claim 91, wherein said member of said mycobacteria comprises at least one member of the *Mycobacterium kansasii*.

95. The method of claim 91, wherein said member of said mycobacteria comprises at least one member of the *Mycobacterium fortuitum* complex.

96. A method of culturing a specimen or extract thereof that is suspected of containing a microorganism having mycolic acid structures in its outer membrane, said method comprising:
a. adding said specimen or extract thereof to culture media that comprises one or more lytic enzymes, wherein said one or more lytic enzymes are active against gram positive bacteria, gram negative bacteria, or mycologic organisms,
b. culturing said specimen suspected of containing said microorganisms using said culture media, wherein said culturing selectively lowers or eliminates levels of microorganisms in said specimen or extract thereof that do not contain mycolic acid structures in their outer membrane relative to the level of microorganisms in said specimen or extract thereof that do contain mycolic acid structures in their outer membrane, and wherein said microorganisms containing mycolic acid structures in their outer membrane retain viability.

97. The method of claim 96 wherein, wherein at least one said lytic enzyme in said composition is selected from the group consisting of an agarase, amidase, aminidase, arabinosidase, cellulase, chitinase, dextranase, dextrinase, fructofuranosidase, fructosidase, fucoidanase, fucosidase, furanosidase, galactanase, galactosidase, galacturonase, galacturonosidase, glucanase, glucosidase, glucanohydrolase, glucohydrolase, glucuronidase, glycanase, glycosidase, laminarinase, lichenase, mannanase, mannosidase, pectinase, peptidase, polysaccharase, protease, proteinase, pullulanase, rhamnosidase, trehalase, xylanase, and xylosidase.

98. The method of claim 96, wherein said lytic enzymes comprise at least one said lytic enzyme in said composition that is a Achromobacter, Arthrobacter, Aspergillus, Bacillus, Brevibacterium, Cytophaga, Flavobacterium, Micromonospora, Oerskovia, Penicillium, Rhizoctonia, Staphylococcus, Streptomyces, or Trichoderma lytic enzyme.

99. The method of claim 96, wherein said method further comprises the addition of a reducing agent before, during and/or after the addition of said one or more lytic enzymes.

100. The method of claim 96, wherein said method further comprises the addition of a betaine-like detergent before, during and/or after the addition of said one or more lytic enzymes.

101. The method of claim 100, wherein said betaine-like detergent is selected from the group consisting of CB-like, SB-like, HSB-like, PB-like, StB-like, PhB-like, SoB-like, RevB-like, AO-like, cAB-like, and ImB-like detergents.

102. The method of claim 101, wherein said betaine-like detergent is a CB-like detergent.

103. The method of claim 102, wherein said CB-like detergent has the structure

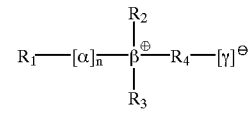

wherein $R_1$ is $C_8$–$C_{22}$;
α is —$CH_2$—, —$CH(OH)$—, —$(CO)$—$NH$—$CH_2CH_2CH_2$—, —O—, or —$C(O)$—;
n is 0 or 1;
β is —$N\oplus$—, —$P\oplus$—, or —$S\oplus$—;
$R_2$ is —H, —$CH_3$, —$C_2H_5$, —$C_3H_7$, or —$C_4H_9$;
$R_3$ is —H, —$CH_3$, —$C_2H_5$, —$C_{31}H_7$, or —$C_4H_9$;
$R_4$ is —$CH_2$—, —$C_2H_4$—, —$C_3H_6$—, —$C_4H_8$—, —$C_5H_{10}$—, —$C_6H_{12}$—, —$CH_2$—$C_6H_4$—, —$C_mH_{2m}$—, —$CH(OH)CH_2CH_2$—, —$CH_2CH(OH)CH_2$—, or —$C_mH_{2m-1}(OH)$— where m is $\geq 1$; and
γ is —$COO\ominus$.

104. The method of claim 103, wherein said CB-like detergent is selected from the group consisting of N-(carboxymethyl)-N,N-dimethyl-1-hexadecanaminium, inner salt (CAS® No. 693-33-4),
cococarboxymethylbetaine and (CAS® No. 68424-94-2),
N-(carboxymethyl)-N,N-dimethyl-9-octadecen-1-aminium, inner salt (CAS® No. 871-37-4),
N-(carboxymethyl)-N,N-dimethyl-3-((1-oxooctadecyl) amino)-1-propanaminium, inner salt (CAS® No. 6179-44-8),
3-amino-N(carboxymethyl)-N,N-dimethyl-1-propanaminium -C8-C22 acyl derivatives, inner salt (CAS® No. 84082-44-0),
N-(carboxymethyl)-3-((12-hydroxy-1-oxo-9-octadecenyl)amino)-N,N-dimethyl-1-propanaminium, inner salt (CAS® No. 71850-81-2), cocoamidopropyl carboxymethylbetaine (CAS® No. 61789-39-7 and CAS® No. 61789-40-0),
N-(2-carboxyethyl)-N,N-dimethyl-1-dodecanaminium, inner salt (CAS® No. 16527-85-8),
N-(2-carboxyethyl)-N,N-dimethyl-1-tridecanaminium, inner salt (CAS® No. 132621-79-5),
N-(2-carboxyethyl)-N,N-dimethyl-1-tetradecanaminium, inner salt (CAS® No. 69725-38-3),
N-(2-carboxyethyl)-N,N-dimethyl-1-hexadecanaminium, inner salt (CAS® No. 42416-43-3),
N-(2-carboxyethyl)-N,N-dimethyl-1-octadecanaminium, inner salt (CAS® No. 30612-73-8),
N-dodecyl-beta-alanine (CAS® No. 1462-54-0),
N-(3-carboxypropyl)-N,N-dimethyl-1-undecanaminium, inner salt (CAS® No. 150147-53-8),
N-(3-carboxypropyl)-N,N-dimethyl-1-dodecanaminium, inner salt (CAS® No. 15163-30-1),
N-(3-carboxypropyl)-N,N-dimethyl-1-tetradecanaminium, inner salt (CAS® No. 146959-90-2),
N-(3-carboxypropyl)-N,N-dimethyl-1-pentadecanaminium, inner salt (CAS® No. 146959-91-3),
N-(3-carboxypropyl)-N,N-dimethyl-1-hexadecanaminium, inner salt (CAS® No. 71695-32-4),
N-(3-carboxypropyl)-N,N-dimethyl-1-octadecanaminium, inner salt (CAS® No. 78195-27-4),
N-(4-carboxybutyl)-N,N-dimethyl-1-dodecanaminium, inner salt (CAS® No. 120139-51-7),
N-(5-carboxypentyl)-N,N-dimethyl-1-dodecanaminium, inner salt (CAS® No. 76392-97-7),
N-(5-carboxypentyl)-N,N-dimethyl-1-hexadecanaminium, inner salt (CAS® No. 73565-98-7),
N-(6-carboxyhexyl)-N,N-dimethyl-1-dodecanaminium, inner salt (CAS® No. 132621-80-8),
4-carboxy-N-dodecyl-N,N-dimethyl-benzenemethanaminium, inner salt (CAS® No. 71695-31-3),
2-carboxy-N-dodecyl-N,N-dimethyl-benzenemethanaminium, inner salt (CAS® No. 71695-34-6),
4-carboxy-N-hexadecyl-N,N-dimethyl-benzenemethanaminium, inner salt (CAS® No. 71695-33-5),
2-carboxy-N-hexadecyl-N,N-dimethyl-benzenemthanaminium inner salt (CAS® No. 71695-35-7),
tallow glycinate (CAS® No. 70750-46-8),
soyamidopropyl carboxymethylbetaine, and
babassuamidopropyl carboxymethylbetaine.

105. The method of claim 104, wherein said CB-like detergent is selected from the group consisting of N-(2-carboxyethyl)-N,N-dimethyl-1-dodecanaminium, inner salt (CAS® No. 16527-85-8),
N-(2-carboxyethyl)-N,N-dimethyl-1-tridecanaminium, inner salt (CAS® No. 132621-79-5),
N-(2-carboxyethyl)-N,N-dimethyl-1-tetradecanaminium, inner salt (CAS® No. 69725-38-3),
N-(2-carboxyethyl)-N,N-dimethyl-1-hexadecanaminium, inner salt (CAS® No. 42416-43-3),
N-(2-carboxyethyl)-N,N-dimethyl-1-octadecanaminium, inner salt (CAS® No. 30612-73-8),
N-(3-carboxypropyl)-N,N-dimethyl-1-undecanaminium, inner salt (CAS® No. 150147-53-8),
N-(3-carboxypropyl)-N,N-dimethyl-1-dodecanaminium, inner salt (CAS® No. 15163-30-1),
N-(3-carboxypropyl)-N,N-dimethyl-1-tetradecanaminium, inner salt (CAS® No. 146959-90-2),
N-(3-carboxypropyl)-N,N-dimethyl-1-pentadecanaminium, inner salt (CAS® No. 146959-91-3),
N-(3-carboxypropyl)-N,N-dimethyl-1-hexadecanaminium, inner salt (CAS® No. 71695-32-4),
N-(3-carboxypropyl)-N,N-dimethyl-1-octadecanaminium, inner salt (CAS® No. 78195-27-4), and
N-(4-carboxybutyl)-N,N-dimethyl-1-dodecanaminium, inner salt (CAS® No. 120139-51-7).

106. The method of claim 105, wherein said carboxybetaine is N-(3-carboxypropyl)-N,N-dimethyl-1-octadecanaminium, inner salt (CB-18) (CAS® No. 78195-27-4).

107. The method of claim 101, wherein said betaine-like detergent is an SB-like detergent.

108. The method of claim 107, wherein said SB-like detergent is SB-18.

109. The method of claim 96, wherein said method further comprises the addition of one or more antibiotics before, during and/or after addition of said one or more lytic enzymes.

110. The method of claim 96, wherein said bacteria is a member of the mycobacteria.

111. The method of claim 110, wherein said member of said mycobacteria comprises at least one member of the *Mycobacterium tuberculosis* complex, *Mycobacterium avium* complex, *Mycobacterium kansasii*, or *Mycobacterium fortuitum* complex.

112. The method of claim 111, wherein said member of said mycobacteria comprises at least one member of the *Mycobacterium tuberculosis* complex.

113. The method of claim 111, wherein said member of said mycobacteria comprises at least one member of the *Mycobacterium avium* complex.

114. The method of claim 111, wherein said member of said mycobacteria comprises at least one member of the *Mycobacterium kansasii*.

115. The method of claim 111, wherein said member of said mycobacteria comprises at least one member of the *Mycobacterium fortuitum* complex.

116. The method of any one of claims 96–115, wherein said culture media is liquid media.

117. The method of any one of claims 96–115, wherein said culture media is solid media.

* * * * *